United States Patent
Fan et al.

(10) Patent No.: US 10,214,713 B2
(45) Date of Patent: Feb. 26, 2019

(54) APPARATUSES AND METHODS FOR HIGH-THROUGHPUT PROTEIN SYNTHESIS

(71) Applicant: UNIVERSITY OF FLORIDA RESEARCH FOUNDATION, INCORPORATED, Gainesville, FL (US)

(72) Inventors: Zhonghui Hugh Fan, Gainesville, FL (US); Kirsten Marie Jackson, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 324 days.

(21) Appl. No.: 14/905,535

(22) PCT Filed: Jul. 17, 2014

(86) PCT No.: PCT/US2014/046958
§ 371 (c)(1),
(2) Date: Jan. 15, 2016

(87) PCT Pub. No.: WO2015/009893
PCT Pub. Date: Jan. 22, 2015

(65) Prior Publication Data
US 2016/0168526 A1    Jun. 16, 2016

Related U.S. Application Data

(60) Provisional application No. 61/847,622, filed on Jul. 18, 2013.

(51) Int. Cl.
*B01J 19/24* (2006.01)
*C12M 1/00* (2006.01)
(Continued)

(52) U.S. Cl.
CPC .......... *C12M 29/04* (2013.01); *B01J 19/2475* (2013.01); *C07K 14/001* (2013.01);
(Continued)

(58) Field of Classification Search
CPC . B01J 19/2475; B01J 2219/24; C07K 14/001; C12M 23/12; C12M 29/04; C12N 9/2402; C12P 19/34
See application file for complete search history.

(56) References Cited

U.S. PATENT DOCUMENTS

| | | | |
|---|---|---|---|
| 5,135,853 A * | 8/1992 | Dziewulski | ............ C12M 23/34 435/243 |
| 5,962,250 A | 10/1999 | Gavin et al. | |

(Continued)

OTHER PUBLICATIONS

Wang, S-J. et al., Chapter 6. Bioreactor Engineering, in Bioprocessing for value Added Products from Renewable Resources, pp. 131-161 (Year: 2007).*

(Continued)

*Primary Examiner* — Teresa E Strzelecka
(74) *Attorney, Agent, or Firm* — Alston & Bird LLP

(57) ABSTRACT

The current is directed to a device comprising, a reaction chamber where a reaction takes place, one or more feeding chambers which contain feeding solution comprising chemicals required for the reaction, and one or more porous membranes separating the reaction chamber from the one or more feeding chambers, and wherein the one or more porous membranes are in substantially vertical position. The current invention is also directed to an apparatus comprising a plurality of devices, wherein each device comprises of a reaction chamber where a reaction takes place, one or more feeding chambers which contain feeding solution comprising chemicals required for the reaction, and one or more porous membranes which separate the reaction chamber from feeding chambers, wherein the one or more porous membranes are in substantially vertical position. These devices and apparatuses can be used for high throughput synthesis of biomolecules and chemicals and biological screening assays.

28 Claims, 20 Drawing Sheets

(51) Int. Cl.
  *C12M 1/32* (2006.01)
  *C07K 14/00* (2006.01)
  *C12N 9/24* (2006.01)
  *C12P 19/34* (2006.01)
  *C07H 21/02* (2006.01)

(52) U.S. Cl.
  CPC ........... *C12M 23/12* (2013.01); *C12N 9/2402* (2013.01); *C12P 19/34* (2013.01); *B01J 2219/24* (2013.01); *C12Y 302/01031* (2013.01)

(56) References Cited

U.S. PATENT DOCUMENTS

| | | |
|---|---|---|
| 6,607,910 B1 | 8/2003 | Dimitrijevich et al. |
| 2003/0213740 A1 | 11/2003 | Creasey |
| 2007/0215538 A1 | 9/2007 | Periana et al. |
| 2011/0081677 A1 | 4/2011 | Luo et al. |

OTHER PUBLICATIONS

International Search Report and Written Opinion dated Oct. 8, 2014 for Application No. PCT/US2014/046958.
International Preliminary Report on Patentability dated Jan. 28, 2016 for Application No. PCT/US2014/046958.
Angenendt et al., Cell-free protein expression and functional assay in nanowell chip format. Anal Chem. Apr. 1, 2004;76(7):1844-9.
Avenaud et al., Expression and activity of the cytolethal distending toxin of Helicobacter hepaticus. Biochem Biophys Res Commun. Jun. 4, 2004;318(3):739-45.
Calhoun et al., Energizing cell-free protein synthesis with glucose metabolism. Biotechnol Bioeng. Jun. 5, 2005;90(5):606-13.
Cappaccio et al., Cell-free co-expression of functional membrane proteins and apolipoprotein, forming soluble nanolipoprotein particles. Mol Cell Proteomics. Nov. 2008;7(11):2246-53. doi: 10.1074/mcp.M800191-MCP200. Epub Jul. 4, 2008.
Chen et al., Cloning, expression, and identification of a novel class IIa bacteriocin in the *Escherichia coli* cell-free protein expression system. Biotechnol Lett. Feb. 2012;34(2):359-64. doi: 10.1007/s10529-011-0779-1. Epub Oct. 22, 2011.
Chueh et al., Leakage-free bonding of porous membranes into layered microfluidic array systems. Anal Chem. May 1, 2007;79(9):3504-8. Epub Aug. 15, 2008.
Hahn et al., A continuous-exchange cell-free protein synthesis system fabricated on a chip. Anal Biochem. Jun. 15, 2007;365(2):280-2. Epub Mar. 25, 2007.
He et al., From DNA to protein: No living cells required. Process Biochem. Mar. 2011;46:615-20. doi:10.1016/j.procbio.2010.11.003.
He et al., Printing protein arrays from DNA arrays. Nature Methods. Jan. 20, 2008;5:175-7. doi:10.1038/nmeth.1178.
He, Cell-free protein synthesis: applications in proteomics and biotechnology. N Biotechnol. Oct.-Dec. 2008 ;25(2-3):126-32. doi: 10.1016/j.nbt.2008.08.004. Epub Aug. 20, 2008. Review.
Jewett et al., Mimicking the *Escherichia coli* cytoplasmic environment activates long-lived and efficient cell-free protein synthesis. Biotechnol Bioeng. Apr. 5, 2004;86(1):19-26. Epub Feb. 12, 2004. 8 pages.
Jewett et al., Substrate replenishment extends protein synthesis with an in vitro translation system designed to mimic the cytoplasm. Biotechnol Bioeng. Aug. 20, 2004;87(4):465-71. doi: 10.1002/bit.20139. Epub Jul. 22, 2004. 8 pages.
Katzen et al., The past, present and future of cell-free protein synthesis. Trends Biotechnol. Mar. 2005;23(3):150-6.
Khnouf et al., Cell-free expression of soluble and membrane proteins in an array device for drug screening. Anal Chem. Aug. 15, 2010;82(16):7021-6. doi: 10.1021/ac1015479.
Khnouf et al., Miniaturized fluid array for high-throughput protein expression. Biotechnol Prog. Nov.-Dec. 2010;26(6):1590-6. doi: 10.1002/btpr.474.

Kigawa, Analysis of protein functions through a bacterial cell-free protein expression system. Methods Mol Biol. 2010;607:53-62. doi: 10.1007/978-1-60327-331-2_6.
Kim et al., A semicontinuous prokaryotic coupled transcription/translation system using a dialysis membrane. Biotechnol Prog. Sep.-Oct. 1996;12(5):645-9.
Kim et al., Prolonging cell-free protein synthesis by selective reagent additions. Biotechnol Prog. May-Jun. 2000;16(3):385-90.
Kim et al., Prolonging cell-free protein synthesis with a novel ATP regeneration system. Biotechnol Bioeng. 1999;66(3):180-8.
Kubick et al., Chapter 2: In Vitro Synthesis of Posttranslationally Modified Membrane Proteins. Current Topics in Membranes. 2009;63:25-49. doi:10.1016/S1063-5823(09)63002-7.
Mei et al., Cell-free protein synthesis in microfluidic array devices. Biotechnol Prog. Nov.-Dec. 2007;23(6):1305-11. Epub Oct. 9, 2007.
Mei et al., Ricin Detection by Biological Signal Amplification in a Well-in-a-Well Device. Anal Chem. Oct. 14, 2006;78(22):7659-64. doi: 10.1021/ac0610006.
Mei et al., Toxin Detection by a Miniaturized in Vitro Protein Expression Array. Anal Chem. Aug. 6, 2005;77(17):5494-500. doi: 10.1021/ac050654w.
Michel-Reydellet et al., Amino acid stabilization for cell-free protein synthesis by modification of the *Escherichia coli* genome. Metab Eng. Jul. 2004;6(3):197-203.
Morita et al., A wheat germ cell-free system is a novel way to screen protein folding and function. Protein Sci. Jun. 2003;12(6):1216-21. doi: 10.1110/ps.0241203.
Nakano et al., Cell-free protein synthesis systems. Biotechnol Adv. Mar. 1998;16(2):367-84.
Nakano et al., Efficient coupled transcription/translation from PCR template by a hollow-fiber membrane bioreactor. Biotechnol Bioeng. Jul. 20, 1999;64(2):194-9.
Ohashi et al., Efficient protein selection based on ribosome display system with purified components. Biochem Biophys Res Commun. Jan. 5, 2007;352(1):270-6. Epub Nov. 13, 2006.
Osaki et al., Lipid-Coated Microdroplet Array for in Vitro Protein Synthesis. Anal Chem. Mar. 18, 2011;83(8):3186-91. doi: 10.1021/ac2000048.
Park et al., A cell-free protein-producing gel. Nature Mater. Mar. 29, 2009;8:432-7. doi:10.1038/nmat2419.
Ryabova et al., Continuous-flow cell-free translation, transcription-translation, and replication-translation systems. Methods Mol Biol. 1998;77:179-93. Review.
Sawasaki et al., A cell-free protein synthesis system for high-throughput proteomics. Proc Natl Acad Sci USA. Nov. 12, 2002;99(23):14652-7. doi: 10.1073/pnas.232580399.
Shimizu et al., Cell-free translation reconstituted with purified components. Nat Biotechnol. Aug. 1, 2001;19:751-5. doi:10.1038/90802.
Shimizu et al., Cell-free translation systems for protein engineering. FEBS J. Sep. 2006;273(18):4133-40. Epub Aug. 23, 2006.
Shimizu et al., Protein synthesis by pure translation systems. Methods. Jul. 2005;36(3):299-304.
Shimizu et al., Chapter 2: PURE Technology. Cell-Free Protein Production: Methods and Protocols. Endo et al., ed. Humana Press, New York. 2010;2:11-21.
Shirokov et al., Chapter 8: Continuous-Flow and Continuous-Exchange Cell-Free Translation Systems and Reactors. Cell-Free Translation Systems. Spirin, ed. Springer, Berlin. 2002; 91-107.
Spirin et al., A continuous cell-free translation system capable of producing polypeptides in high yield. Science. Nov. 25, 1988;242(4882):1162-4.
Spirin et al., Chapter 1: Cell-Free Protein Synthesis Systems: Historical Landmarks, Classification, and General Methods. Cell-Free Protein Synthesis: Methods and Protocols. Spirin, ed. Wiley-VCH Verlag GmbH & Co. KGaA, Weinheim. Jul. 2008;1:1-34.
Spirin, High-throughput cell-free systems for synthesis of functionally active proteins. Trends Biotechnol. Oct. 2004;22(10):538-45.
Stögbauer et al., Experiment and mathematical modeling of gene expression dynamics in a cell-free system. Integr Biol. Apr. 5, 2012;4:494-501. doi: 10.1039/C2IB00102K.

(56) References Cited

OTHER PUBLICATIONS

Structural Genomics Consortium et al., Protein production and purification. Nat Methods. Feb. 2008;5(2):135-46. doi: 10.1038/nmeth.f.202. Review. Epub Sep. 22, 2011.

Svitkin et al., A highly efficient and robust in vitro translation system for expression of picornavirus and hepatitis C virus RNA genomes. Methods Enzymol. 2007;429:53-82.

Tawfik et al., Man-made cell-like compartments for molecular evolution. Nat Biotechnol. Jul. 1998;16(7):652-6.

Teh et al., Stable, biocompatible lipid vesicle generation by solvent extraction-based droplet microfluidics. Biomicrofluidics. Dec. 2011;5(4):044113.1-12. doi: 10.1063/1.3665221.

Watanabe et al., Cell-free protein synthesis for structure determination by X-ray crystallography. Methods Mol Biol. 2010;607:149-60. doi: 10.1007/978-1-60327-331-2_13.

Wu et al., A PMMA microfluidic droplet platform for in vitro protein expression using crude *E. coli* S30 extract. Lab Chip. 2009;9:3391-8. doi: 10.1039/B911581A.

\* cited by examiner

A  B

APPARATUSES AND METHODS FOR HIGH-THROUGHPUT PROTEIN SYNTHESIS

CROSS-REFERENCE TO RELATED APPLICATION

This application is a national stage filing under 35 U.S.C. § 371 of International Application No. PCT/US2014/046958 with an international filing date of Jul. 17, 2014, which claims the benefit of U.S. Provisional Application Ser. No. 61/847,622 filed Jul. 18, 2013, the entire contents of which are hereby incorporated by reference in their entireties, including all figures, table and amino acid or nucleic acid sequences.

This invention was made with government support under OISE-0968313 awarded by National Science Foundation. The government has certain rights in the invention.

BACKGROUND OF THE INVENTION

Advances in automation and high throughput technologies have made it possible to perform high throughput synthesis and testing of molecules, for example, biomolecules and drugs. Commonly used apparatuses for high throughput synthesis and screening involve use of multi-well plates or micro-plates. Conventional multi-well plates and apparatuses provide limited supply of reagents which do not provide highly efficient synthesis of the products.

A continuous exchange format multi-well plate provides higher yields of the products synthesized in a high throughput manner because it allows for constant supply of chemicals required for the synthesis reaction and removal of inhibitory byproducts through porous membranes. An example of continuous exchange format multi-well plate is shown in FIG. 1B where the porous membrane is present in horizontal orientation. In the horizontal orientation, heavy molecules in the reaction mixture, for example aggregated proteins or ribosome in case of cell free protein synthesis, can settle down on the membrane, thereby blocking the membrane pores and hampering exchange of chemicals and inhibitory byproducts which in turn inhibits the reaction taking place in the reaction mixture.

Further, prior art multi-well devices also suffer from inconsistency and lack of uniformity between the reaction mixtures in different wells. For example, differences in the reagent concentrations in different wells of a multi-well apparatus can affect the results of the high throughput screening.

BRIEF SUMMARY OF THE INVENTION

The current invention provides a continuous exchange format multi-well apparatuses wherein the porous membranes are oriented vertically as shown in FIG. 1C. With the porous membrane in vertical position, large molecules in the reaction mixture settle at the bottom of the reaction chamber, eliminating membrane blockage and thereby increasing the rate of reaction. The current invention also provides apparatuses for carrying out multiple reactions wherein each reaction occurs in presence of same reagent mixture thereby avoiding well to well variance and providing higher uniformity and consistency of reactions in a high throughput assay.

Various aspects of the current invention provide a device comprising, a reaction chamber, one or more feeding chambers which contain feeding solution(s) comprising chemicals required for the reaction, and one or more porous membranes which separate the reaction chamber from said one or more feeding chambers. The porous membrane(s) allow the passage of chemicals between the reaction chamber and said one or more feeding chambers and prevent passage of other chemicals between the reaction chamber and the feeding chambers. The passage of certain chemicals between the reaction chamber and the one or more feeding chambers comprises the passage of chemicals required for the reaction from the feeding chamber to the reaction chamber and the passage of the reaction by-products from the reaction chamber to the feeding chamber. In certain embodiments, the porous membranes in the apparatuses provided herein are in a substantially vertical position.

Another aspect of the invention provides for apparatuses for high throughput synthesis of products or high throughput screening assays. These apparatuses comprise of a plurality of devices, wherein each device comprises a reaction chamber where a reaction takes place, one or more feeding chambers which contain feeding solution comprising chemicals required for the reaction, and one or more porous membranes which separate the reaction chamber from the one or more feeding chambers. The porous membrane(s) allow the passage of certain chemicals between the reaction chamber and the one or more feeding chambers and prevent passage of other chemicals between the reaction chamber and the one or more feeding chambers. In certain embodiments, the porous membranes in the apparatuses of the current invention are in substantially vertical position.

The apparatuses can be modified for high throughput synthesis of products, for example, drugs, nucleic acids, or proteins. Alternatively, the apparatuses can also be modified for high throughput screening assays, for example, enzyme inhibition assays or drug screening assays. The apparatuses disclosed herein provide higher yields of the synthesized products and minimize costs of starting materials. The apparatuses can also be modified for high throughput studying of the reaction conditions, for example, by varying the reaction components and/or reaction conditions in each well. The apparatuses can also be modified for high throughput protein structure analysis, for example, by determining structures of proteins synthesized in each well using x-ray cystography. The apparatuses can also provide uniform reaction conditions between different reaction chambers amongst the plurality of devices thereby providing consistency and uniformity of the results.

DETAILED DISCLOSURE OF THE INVENTION

Figure 1:
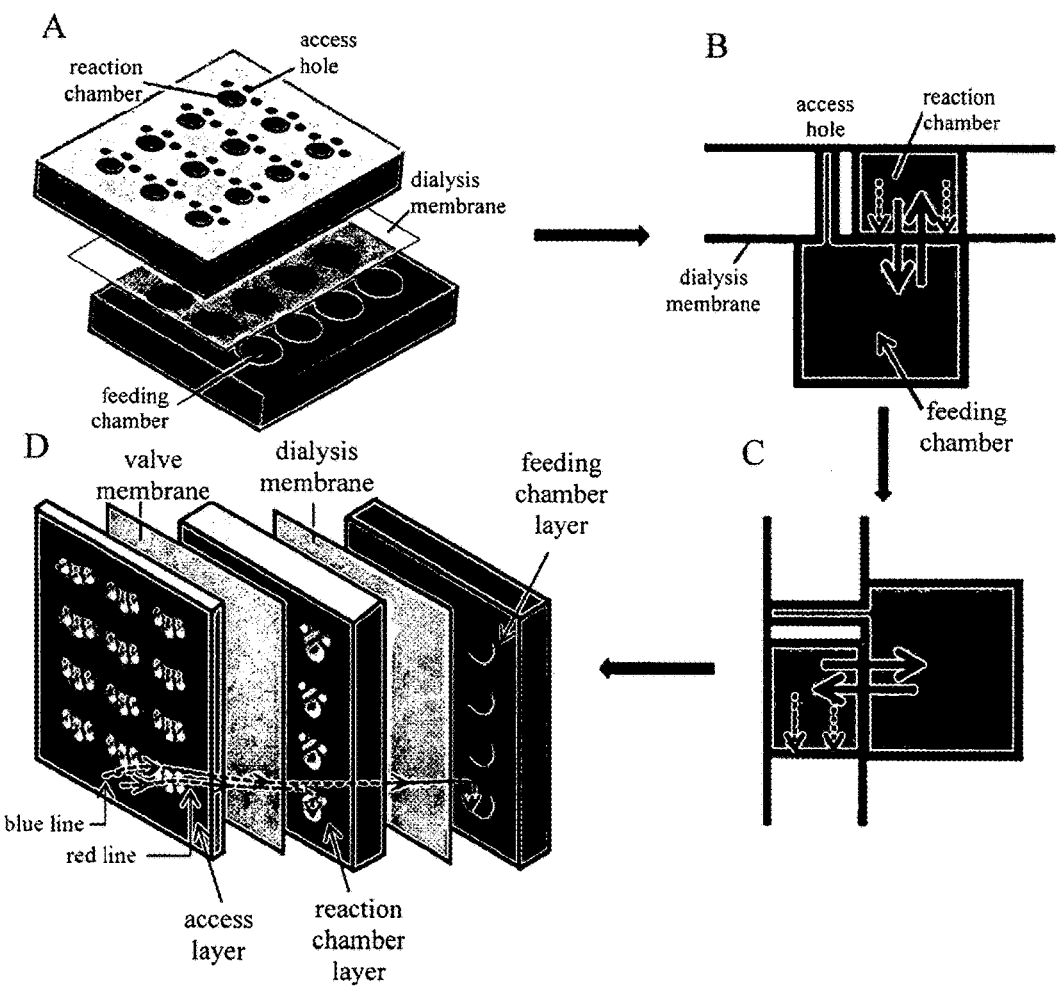
FIGS. 1A-1D. A. Exploded diagram of the Horizontal Apparatus consisting of three layers: reaction chamber layer, dialysis membrane, and feeding chamber layer. The access holes are for dispensing a solution into the feeding chamber. An array of 3×4 wells is illustrated here for clarity and simplicity, though other array formats such as 8×12 wells can be easily made. B. Cross-sectional view of one well in A. The dialysis membrane is horizontally oriented, resulting in possible sedimentation of large molecules on the membrane as indicated by dashed red arrows. The solid block (black) arrows connecting the reaction chamber and the feeding chamber (FIGS. 1B and 1C) indicate the exchange of small molecules between two chambers. C. Rotation of B by 90° and the dialysis membrane is oriented vertically. Thus large molecules may settle down on the bottom of the reaction chamber, but not on the membrane. D. Exploded diagram of Vertical Apparatus I designed according to C. It consists of five layers as indicated (access layer, valve membrane, reaction chamber layer, dialysis membrane and feeding chamber layer). The dashed red and blue lines depict the movement of the reaction and feeding solutions, respectively. The solutions follow the horizontal portion of the lines when they are filled into the device placed horizontally, and then they fall down to the bottom portion of the wells (as indicated by the vertical portion of the lines at the end) when the device is placed vertically. The diagrams are not to scale.

The term "about" is used in this patent application to describe some quantitative aspects of the invention, for example, concentration of chemicals, dimensions, volumes or time of contact. It should be understood that absolute accuracy is not required with respect to those aspects for the invention to operate. When the term "about" is used to describe a quantitative aspect of the invention the relevant aspect may be varied by up to ±10%. Thus, these values can vary by ±1%, ±2%, ±3%, ±4%, ±5%, ±6%, ±7%, ±8%, ±9% or ±10%.

A first aspect of the invention provides a device comprising, a reaction chamber where a reaction takes place, one or more feeding chambers containing feeding solution comprising chemicals required for the reaction, and one or more porous membranes separating the reaction chamber and the one or more feeding chambers. The porous membrane(s) allow passage of certain chemicals between the reaction chamber and said one or more feeding chambers and prevents passage of other chemicals between the reaction chamber and the feeding chamber(s). In particular embodiments, the porous membrane(s) may be in a substantially vertical position. A porous membrane in a substantially vertical position is positioned at an angle of about 0 degrees to about 30 degrees corresponding to the vertical plane, preferably between about 0 degrees and 10 degrees from the vertical plane of the reaction chamber. The device disclosed herein can provide a single reaction chamber or a plurality of reaction chambers, each of which can be connected to one or more feeding chamber.

The porous membrane(s) separating the feeding chamber(s) and the reaction chamber can be semipermeable. Examples of semipermeable membranes include, but are not limited to, nanoporous membranes, lipid membranes, and dialysis membranes (e.g. cellophane). Additional examples of semipermeable membranes are well known to a person of ordinary skill in the art and are within the purview of this invention.

The materials of porous membranes can be cellulose, cellulose acetate, nitrocellulose, cellulose esters, polycarbonate, polysulfone, polyether sulfone, polyacrylonitrile, polyamide, polyimide, polyethylene, polypropylene, polytetrafluoroethylene, polyvinylidene fluoride, polyvinylchloride, and other polymeric membranes.

Semipermeable membranes allow passage of certain chemicals while preventing or limiting passage of other chemicals. Non-limiting examples of the semipermeable membranes include size based semipermeable membranes, charge based semipermeable membranes, anion exchange membranes, alkali anion exchange membranes, charge mosaic membranes, and proton exchange membranes.

Passage of chemicals between the reaction chamber and the feeding chambers can occur through a variety of mechanisms. For example, diffusion can be one of the mechanisms to transport materials between two chambers. Diffusion of each compound results from the difference in its concentration in two chambers. Osmosis can be an additional mechanism resulting from the salt concentration difference between two chambers. Additional mechanisms include hydrostatic pressure and other external forces to drive materials from one side to the other side of a membrane. Further mechanisms allowing passage of chemicals between the reaction chamber and the feeding chambers are known to a person of ordinary skill in the art and are within the purview of this invention.

Size based semipermeable membranes allow passage of molecules smaller than a particular size while preventing passage of molecules larger than a particular size. For example, a semipermeable membrane can allow passage of molecules smaller than about 8000 Daltons whereas preventing passage of molecule larger than about 8000 Daltons.

Charge based semipermeable membranes, for example, anion exchange membranes, alkali anion exchange membranes, charge mosaic membranes, and proton exchange membranes allow passage of molecules carrying a particular charge, for example, positive charge, while preventing passage of molecules carrying the opposite charge.

In a particular embodiment, the level of feeding chamber is higher than the level of the reaction chamber. For example, the height differential ($\Delta h$) can be at least 0.05 mm and less than or equal to 50 mm. In another embodiment of the device, the height differential can be about 0.5 mm to about 5 mm. In another embodiment, the level of feeding chamber is equal to the level of the reaction chamber.

In certain embodiments, the ratio of the volume of said one or more feeding chambers to the volume of said reaction chamber is about 5:1, about 10:1, about 15:1, about 20:1, about 25:1, or about 30:1. The volume of the said reaction chamber ranges from 1 to 100 µL and the volume of the said feeding chamber ranges from 5 to 3000 µL. For example, the volume of said one or more feeding chambers can be about 750 µL to about 25 µL; whereas, the volume of said reaction chamber can be about 25 µL to about 5 µL. In certain embodiments, the volumes of said one or more feeding chambers and said reaction chamber can be about 50 µL and about 10 µL, respectively; about 100 µL and about 10 µL, respectively; about 150 µL and about 10 µL, respectively; about 200 µL and about 10 µL, respectively; about 250 µL and about 10 µL, respectively; or about 300 µL and about 10 µL, respectively. In other embodiments, the volumes of said one or more feeding chambers and said reaction chamber are about 25 µL and 5 about µL, respectively; about 50 µL and about 5 µL, respectively; about 75 µL and about 5 µL, respectively; about 100 µL and about 5 µL, respectively; about 125 µL and about 5 µL, respectively; or about 150 µL and about 5 µL, respectively.

In certain embodiments, the ratio of the volume of said feeding solution to the volume of said reaction mixture is about 5:1, about 10:1, about 15:1, about 20:1, about 25:1, or about 30:1. The volume of the said reaction chamber ranges from 1 to 100 µL and the volume of the said feeding chamber ranges from 5 to 3000 µL. For example, the volume of said feeding solution can be about 750 µL to about 25 µL; whereas, the volume of said reaction mixture can be about 25 µL to about 5 µL. In certain embodiments, the volumes of said feeding solution and said reaction mixture can be about 50 µL and about 10 µL, respectively; about 100 µL and about 10 µL, respectively; about 150 µL and about 10 µL, respectively; about 200 µL and about 10 µL, respectively; about 250 µL and about 10 µL, respectively; or about 300 µL and about 10 µL, respectively. In other embodiments, the volumes of said feeding solution and said reaction mixture are about 25 µL and 5 about µL, respectively; about 50 µL and about 5 µL, respectively; about 75 µL and about 5 µL, respectively; about 100 µL and about 5 µL, respectively; about 125 µL and about 5 µL, respectively; or about 150 µL and about 5 µL, respectively.

As discussed above, the reaction taking place in the reaction chamber of the device can provide for the synthesis of a product. Thus, the device can be modified to synthesize various products, for example, proteins, DNA, RNA, drug molecules, etc. In one embodiment, the reaction taking place in the reaction chamber provides for the synthesis of a protein. The synthesis of the protein can take place through cell free protein synthesis (CFPS). CFPS systems can be prokaryotic or eukaryotic and are available from various vendors (for example the RTS 100 Wheat Germ kit available from Fisher Scientific, Inc. (Pittsburgh, Pa.)). For the synthesis of proteins, the feeding solution provides certain raw materials for CFPS, for example, raw materials for CFPS that are diffusible through the semipermeable membrane and which include, but are not limited to, amino acids, nucleotides, ATP (adenosine triphosphate), GTP (guanosine triphosphate), protease inhibitors, RNase inhibitors, magnesium, potassium, etc. The reaction chamber can contain both raw materials that are diffusible through the semipermeable membrane and other raw materials that are not diffusible through the semipermeable membrane, for example, gene transcription and/or protein synthesis machinery (e.g., DNA, RNA polymerase, 80S ribosomes, eukaryotic or prokaryotic tRNAs, initiation factors, elongation factors, termination factors (release factors), amino acids, NTPs, basic chaperones, ribosome-recycling factors, aminoacyl-tRNA synthetases, methionyl-tRNA transformylase, creatine phosphate, 10-formyl-5,6,7,8-tetrahydrofolic acid, creatine kinase, myokinase, nucleoside-diphosphate kinase, pyrophosphatase, etc.). Components of the gene transcription include, but are not limited to, DNA, ATP, CTP, GTP, UTP, RNA polymerase, etc. Components of the protein synthesis machinery include, but are not limited to, DNA or RNA encoding for the protein to be synthesized, ribosomes, tRNA, amino acids, aminoacyl-tRNA synthetase, translation factor proteins, etc. The semipermeable membranes can be designed to allow passage of raw materials from feeding chamber to the reaction chamber and passage of inhibitory by-products produced during the protein synthesis from reaction chamber to feeding chamber while preventing passage from the reaction chamber to the feeding chamber of larger molecules, for example, components of protein synthesis machinery involved in CFPS and proteins synthesized in the reaction chamber. Further details regarding CFPS using the devices of the current invention are described below in the Materials and Methods section and certain of the examples.

In another embodiment of the invention, the reaction taking place in the reaction chamber provides for the synthesis of nucleic acids, for examples, DNA or RNA. The synthesis of nucleic acids can take place through, for example, gene expression for RNA or polymerase chain reaction (PCR) for DNA. The feeding solution for PCR provides certain raw materials, for example, raw materials that are diffusible through the semipermeable membrane, including but are not limited to, dNTPs, ATP, $MgCl_2$, $MnCl_2$, $K^+$ ions, small molecules used in identification of the synthesized nucleic acids (e.g. fluorescent dyes, ethidium bromide, etc.). The reaction chamber contains other raw materials that are not diffusible through the semipermeable membrane. Such raw materials include, but are not limited to, template nucleic acids, DNA or RNA polymerase, primers for PCR, probes used in identification of synthesized nucleic acids, etc. The semipermeable membranes can be designed to allow passage of raw materials from the feeding chamber to the reaction chamber and passage of inhibitory by-products produced during PCR from the reaction chamber to the feeding chamber while preventing or limiting passage of larger molecules involved in nucleic acid synthesis and the synthesized nucleic acids from reaction chamber to feeding chamber.

In another embodiment of the invention, the reaction taking place in the reaction chamber provides for the synthesis of a drug. One example of such drugs is tissue plasminogen activator (tPA), which is used in diseases that feature blood clots, such as pulmonary embolism, myocardial infarction, and stroke. Another example of such drugs is erythropoietin, with trade names including Epogen/Procrit and Aranesp, which are used in treating anemia resulting from chronic kidney disease and myelodysplasia from the treatment of cancer (chemotherapy and radiation). For the synthesis of drugs, the feeding solution can provide certain raw materials for drug synthesis, for example, raw materials for drug synthesis that are diffusible through the semipermeable membranes. The raw materials provided by the feeding solution and the non-diffusible raw materials present in the reaction chamber depend on the type, size, or charge of the drug produced. For example, if a drug is synthesized through enzymatic process, the feeding solution can provide precursor chemicals, catalysts, cofactors (all of which can be smaller than the size of the drug molecule); whereas, the reaction chamber can provide enzymes required for the drug synthesis. The semipermeable membranes can be designed to allow passage of raw materials from feeding chamber to the reaction chamber and passage of inhibitory by-products produced during the drug synthesis from reaction chamber to feeding chamber while preventing passage of large molecules involved in drug synthesis and the synthesized drugs from the reaction chamber to feeding chamber.

In a further embodiment of the invention, the reaction taking place in the reaction chamber is a bio-assay. Non-limiting examples of bio-assays include enzymatic assays, enzyme inhibition assays, enzyme activation assays, nucleic acid hybridization assays, protein-protein binding/interaction assays, biological screening assays.

In an embodiment of the invention, the bio-assay taking place in the reaction chamber is an enzymatic assay. In such embodiment, the feeding solution can provide substrates, cofactors, enzyme activators or inhibitors; whereas, the reaction chamber can contain the enzyme used in the assay. The semipermeable membranes can be designed to allow passage substrates, cofactors, activators, and inhibitors from the feeding chamber to the reaction chamber and passage of inhibitory by-products produced during the enzymatic assay from the reaction chamber to the feeding chamber, while preventing passage of enzymes and other larger molecules from the reaction chamber to the feeding chamber.

In an embodiment of the invention, the one or more feeding chambers of the device of the current invention can be connected with channels thereby allowing simultaneous addition of liquids to the one or more feeding chambers or simultaneous removal of liquid from the one or more feeding chambers. Interconnecting the one or more feeding chambers also provides a uniform feeding solution for the reaction taking place in the reaction chamber.

Certain aspects of the current invention provide an apparatus comprising a plurality of the devices disclosed in this application. In a particular embodiment, the number of devices present in the apparatus is 3 or 4 or multiples of 3 or 4. In another embodiment of the invention, the apparatus of the current invention comprise of 96 devices. In a further embodiment of the current invention, the number of devices present in the apparatus is multiple of 96. In an even further embodiment of the invention, the apparatus of the current invention comprise 96, 192, 288, 384, 480, 576, 672, 768, 864, 960, or 1536 devices.

As discussed above, one of the products that can be synthesized in an apparatus as disclosed herein is proteins. For example, in an apparatus comprising 96 devices, 96 different types of proteins can be synthesized, i.e. a different type of protein is synthesized in each of the 96 devices. In another embodiment of the invention, different types of proteins are synthesized in the plurality of devices of the apparatus of the current invention; however, a same type of protein is synthesized in multiple devices of the apparatus. For example, in an apparatus comprising of 96 devices, 24 different types of proteins are synthesized and a particular type of protein is synthesized in 4 different devices within the apparatus. Such embodiments allow running replicates of protein synthesis reactions using an apparatus of the current invention, for example, CFPS as disclosed above.

In another embodiment of the invention, proteins may go through modifications such as glycosylation by adding carbohydrates. In another embodiment of the invention, chaperon molecules can be added into the reaction chamber to facilitate proper folding of proteins synthesized. In another embodiment of the invention, lipids or other molecules can be added into the reaction chamber to allow membrane proteins to be synthesized. One example is to synthesize bacteriorhodopsin, lipoprotein, or GPCR (G protein-coupled receptors) in the presence of lipids.

In another embodiment of the invention, the same type of proteins is synthesized in a number of devices while different reaction conditions are used. One application of such schemes is to study the optimum conditions to achieve highest protein synthesis yield by varying the components, component concentrations, temperature, etc. Another application of such schemes is to identify the conditions for protein crystallization and the resulting protein crystals can be used for protein structure studies. Another application of such schemes is to screen possible compound inhibitors for drug discovery. One example is to discover the best beta-lactamase inhibitor for addressing antibiotic resistance.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Methods and Materials
Materials

Polycarbonate sheets were purchased from McMaster-Carr (Atlanta, Ga., USA) with thicknesses of 0.5 and 0.1 inches. Flat sheet porous membranes with a molecular weight cutoff of 6-8 kDa were obtained from Spectrum Labs (Rancho Dominguez, Calif., USA). Sylgard 184 silicone elastomer was attained from Dow Corning (Midland, Mich., USA). Wheat germ RTS100 kits were acquired from 5 Prime (Hamburg, Germany). 4-methylumbelliferyl-β-D-glucuronide (MUG) was purchased from Marker Gene Technologies Inc. (Product Number M240, Eugene, Oreg., USA).

Apparatus Fabrication

Three apparatuses were fabricated using polycarbonate sheets and porous membranes. The first apparatus, referred to as the Horizontal Apparatus, is the same as reported previously.[14] As show in FIG. 1A, it consists of three layers: a reaction chamber layer at the top, a porous membrane in the middle, and a feeding chamber layer at the bottom. The top and bottom layers were machined in 0.5-inch-thick polycarbonate sheets. An array of 3×4 wells was created in the footprint of a 96-well plate. In the top layer, the largest well is a 4.5-mm-diameter reaction chamber and it is surrounded by three 2-mm-diameter access holes connecting to the feeding chambers. The volume of the reaction chamber can be about 79.5 mm$^3$. The feeding chambers on the bottom layer are 12 units of 9-mm-diameter wells; each unit encompasses both reaction chamber and access holes in the top layer. The feeding chambers can have a depth of about 3 mm and a volume of about 188.6 mm$^3$. As illustrated in FIG. 1B, the porous membrane in the middle is to separate the reaction and feeding chambers so that small molecules such as ATP can pass through from the feeding chamber to the reaction chamber whereas proteins synthesized remain in the reaction chamber. The porous membrane at the access hole location was punctured so that the feeding chamber became accessible.

The apparatus referred to as the Vertical Apparatus I (FIG. 1D) was derived from the layout in FIG. 1C, which was obtained by rotating the layout in FIG. 1B by 90°. In Vertical Apparatus I, the porous membrane is oriented vertically. It consists of five layers: an access layer at the top (on the left in FIG. 1D), a valve membrane, a reaction chamber layer in the middle, a porous membrane, and a feeding chamber layer at the bottom. The top layer comprises of 12 units of 3 wells that are 2 mm wide and 3.5 mm long. Among those 3 wells, the well in the center (referred to as reaction access well) provides an access to the reaction chamber in the middle layer, and the other two wells (referred to as feeding access well) provide an access to the feeding chamber in the bottom layer. The valve membrane is designed to prevent the reaction solution from leaking out as discussed later, and we employed a porous membrane for this purpose for fabrication simplicity. In the middle reaction chamber layer, each unit consists of one 4.5-mm-diameter reaction chamber connecting to an extension chamber of 2 mm wide and 2.5 mm long. The middle reaction chamber can have a volume of about 79.5 mm$^3$. This extension chamber aligns with the reaction access well in the top layer and provides a passage that guides the reaction solution downward into the circular reaction area as illustrated by the red dashed arrow in FIG. 1D. Since the valve membrane only at the extension chamber portion is punctured, the reaction solution in the circular reaction portion will not leak out through the access well when the device is oriented vertically for protein synthesis.

As a result, this membrane essentially functions as a valve. There are also two 2-mm-diameter through-holes in the reaction chamber layer, and they are connected to feeding access wells in the top layer and provide an access to the feeding chamber in the bottom layer. The porous membrane in FIG. 1D separates the reaction and feeding chambers and enables the controlled exchange of nutrients and reaction byproducts between the two solutions. The feeding chamber layer is composed of 12 units of 9-mm-diameter feeding chambers that align with the reaction chambers. The feeding chamber layer can have a depth of about 3 mm and a volume of about 188.6 mm$^3$. Appropriate areas in both valve and porous membranes were punctured to access the feeding chamber at the bottom via the feeding access holes in the top. The top layer was machined in a 0.1-inch-thick polycarbonate sheet, and the middle and bottom layers were machined in 0.5-inch-thick polycarbonate sheets.

Figure 2:
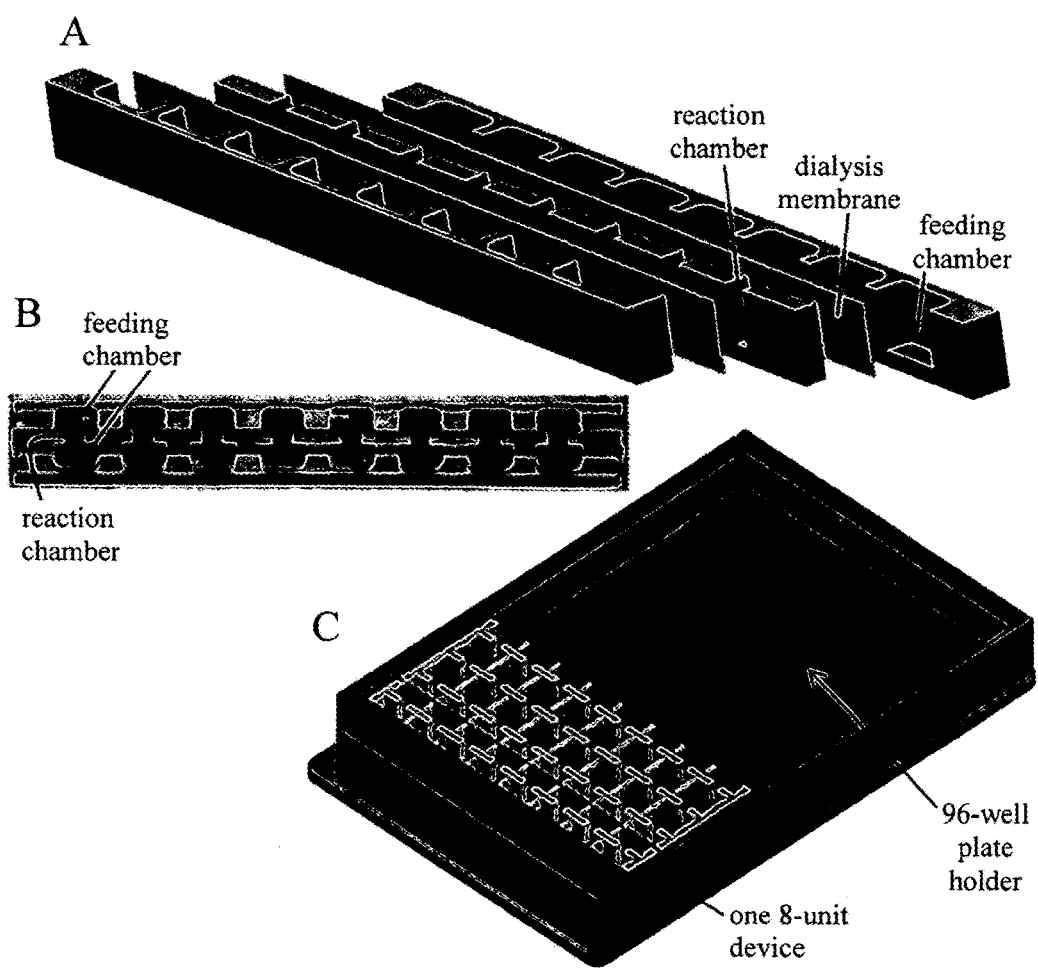
FIGS. 2A-2C. A. Exploded diagram of Vertical Apparatus II consisting of 5 layers to form one reaction chamber in the middle and two feeding chambers on both sides. Two membrane layers are used to separate the reaction chamber from the feeding chambers. The diagram is not to scale. B. Picture (top view) of the 8-unit device in A. The feeding chambers were filled with a red dye solution for easy visualization while the reaction chamber was filled with a blue dye solution. C. Diagram showing 4 of 8-unit Vertical Apparatus II in a 96-well micro-plate holder.

As shown in FIG. 2A, Vertical Apparatus II also consists of five layers: two feeding chamber layers, a middle reaction chamber layer, and two porous membranes. The feeding chamber layers consist of 8 units of feeding chambers with dimensions of 7 mm long, 3 mm wide and 5 mm deep and a volume of about 105 mm$^3$ except for where specified otherwise. The reaction chamber layer comprises 8 units of 2 mm long, 2.5 mm wide and 5 mm deep reaction chambers with a volume of about 50 mm$^3$ that align with the feeding chambers. The location of the reaction chamber is designed according to the standard of a conventional 96-well microplate. The reaction and feeding chambers are separated by two porous membranes. The chamber layers were machined in 0.5-inch-thick polycarbonate sheets. The design of Vertical Apparatus II can be designed to serve as one of 12 apparatuses that can be placed in a micro-plate holder for compatibility with a conventional plate reader for detection. An illustration of this micro-plate holder with four Vertical Apparatus II devices is shown in FIG. 2C.

All apparatuses were assembled using a microstamping technique.[14,29] Briefly, polydimethylsiloxane (PDMS) (Sylgard 184, Dow Corning) was prepared according to the manufacturer's instructions and coated on a substrate using a spinner (Laurell Technologies) at 1500 RPM (revolution per minute) for 15 s. For each apparatus, the surfaces that interact with the porous membranes in the final apparatus were brought into contact with the PDMS on the substrate, transferring a thin layer of PDMS to the polycarbonate surface. The apparatuses were then assembled such that one porous membrane separates each polycarbonate layer coated with PDMS. The assembly was then cured in an oven at 70° C. for four hours and left overnight in room temperature before experiments. A picture of one assembled apparatuses is shown in FIG. 2B.

The fabrication methods described above are used to realize the concept. The actual manufacturing methods to fabricate devices in large quantities include injection molding, compression molding, extrusion, blow molding, thermoforming, rotational molding, casting, foaming, transfer molding, and other plastic manufacturing method.

Protein Synthesis

The RTS100 wheat germ kit was used to synthesize β-glucuronidase (GUS). Other proteins we have synthesized include luciferase, alkaline phosphatase, β-lactamase, β-galactosidase, green fluorescent protein, and chloramphenicol acetyl-transferase. A number of other proteins can be synthesized using CFPS. All of the components necessary for protein synthesis were included in the kit. Following the manufacturer's instructions, the reaction solution consists of 15 μL of wheat germ lysate, 15 μL of the reaction mix, 4 μL of amino acids, 1 μL of methionine, and 15 μL of the GUS control vector (2 μg) in nuclease-free water. The feeding solution is composed of 900 μL of the feeding mix, 80 μL of amino acids, and 20 μL of methionine.

For experiments in a device or an apparatus, 10 μL of the reaction solution and 200 μL of feeding solution were pipetted into the reaction and feeding chambers, respectively. GUS expression in the conventional micro-plate was carried out by pipetting 10 μL of reaction solution into a well of a black 96-well micro-plate. The devices or apparatuses were covered with PCR tape to prevent evaporation and placed on an orbital shaker at 30 RPM for 4 hours except for where specified otherwise. For optimization, the length of reaction time was varied to determine optimal reaction time in the vertically oriented devices. To detect GUS expression in the devices, the product was transferred to a black 96-well micro-plate, and 30 μL of 100 μM MUG was added. The micro-plate was then placed in the Mithras Micro-plate Reader (Berthold Technologies, Germany). After 15 min, the fluorescence was measured for 10 s using a filter with excitation and emission wavelengths of 355 nm and 460 nm, respectively.

To study the movement of solutions between the chambers, two experimental setups were designed. In the first setup, 10 μM of fluorescein (Sigma-Aldrich) was included in the reaction solution while the feeding solution was prepared as described above. The reaction and feeding solutions were then pipetted into the reaction and feeding chambers of the device, respectively, and the device was covered with PCR tape and placed on an orbital shaker at 30 RPM for five hours. After each hour, 2 μL of the feeding solution was removed from the device and its fluorescein concentration was measured by transferring it to a micro-plate. To ensure the well bottom of the micro-plate is covered with sufficient amount of liquid for measurement accuracy, 10 μL of the pure feeding solution was added before measuring fluorescence. The fluorescence was measured for 10 s using the micro-plate reader at excitation and emission wavelengths of 485 and 535 nm, respectively. To maintain the solution level and prevent the additional hydrostatic pressure between two chambers, 2 μL of pure feeding solution was added back into the reaction chamber at each hour. All of these dilution effects were compensated in calculating fluorescein concentrations. The second setup had the same experimental conditions as the first setup except that fluorescein was added to the feeding solution instead of the reaction solution, and 2 μL of the reaction solution was removed each hour for fluorescence measurement.

μFAD Fabrication

Figure 14A:
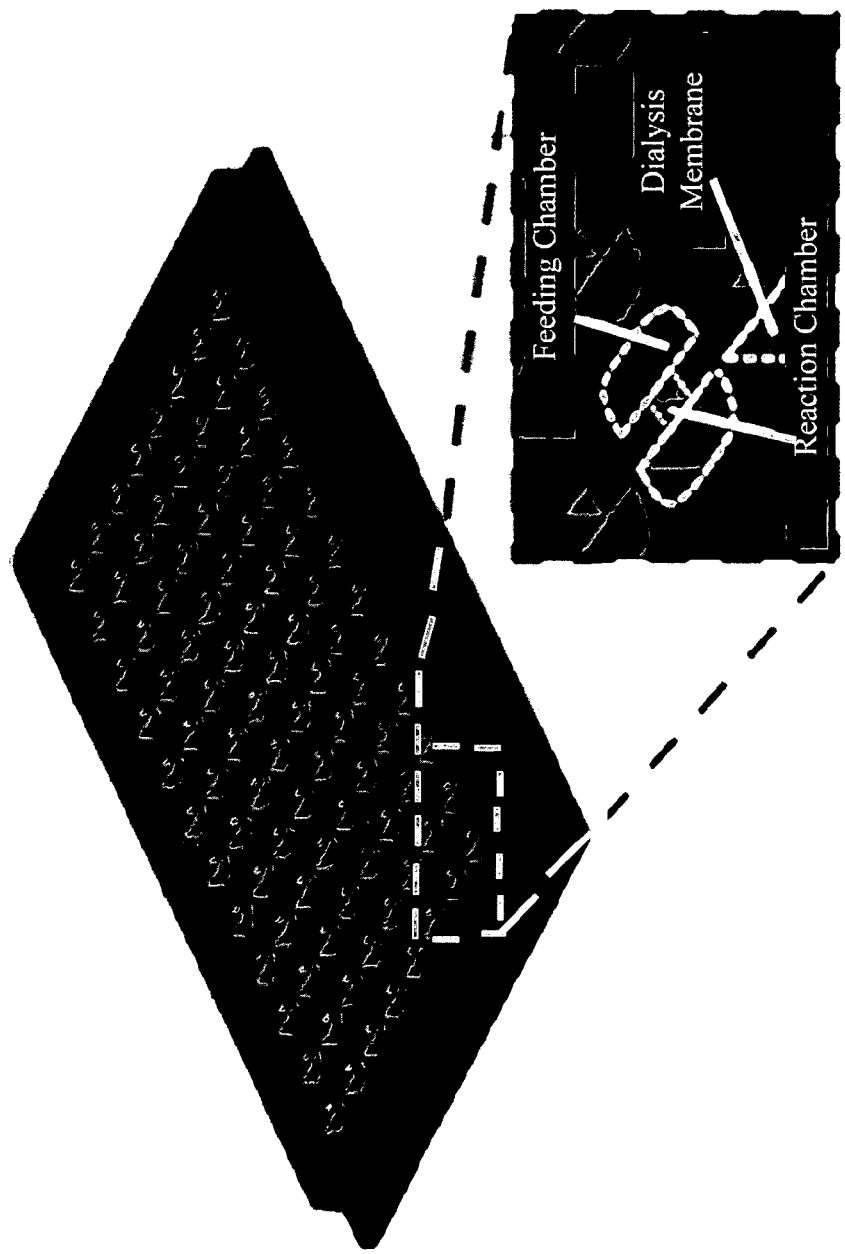
FIGS. 14A-14B. Depiction of a miniaturized fluid array device (μFAD). (A) Three-dimensional rendering of the 96-well μFAD. (Inset): an expanded view of several protein expression units. As labeled, the reaction chamber is isolated from the two feeding chambers by vertically oriented dialysis membranes. (B) Cross-sectional illustration of one protein expression unit of the μFAD. The reaction chamber (central chamber) contains the transcriptional and translational machinery necessary for protein expression along with the synthesized protein. The feeding solution consists of the nutrient and energy molecules needed to sustain protein expression. The solution level in the feeding chamber is higher than that in the reaction chamber, facilitating the replenishment of the nutrients. (Inset): an expanded view showing the different components for the reaction and feeding solutions. Chemical movement of energy/nutrient molecules from the feeding solution to the reaction solution and inorganic phosphate from the reaction solution to the feeding solution is depicted with arrows. The green, red, yellow, purple, blue, and black arrows represent amino acids (AA), GTP, magnesium ions ($Mg^{2+}$), creatine phosphate (CP), ATP, and inorganic phosphate ($P_i$), respectively. The drawing is not to scale.
Figure 14B:
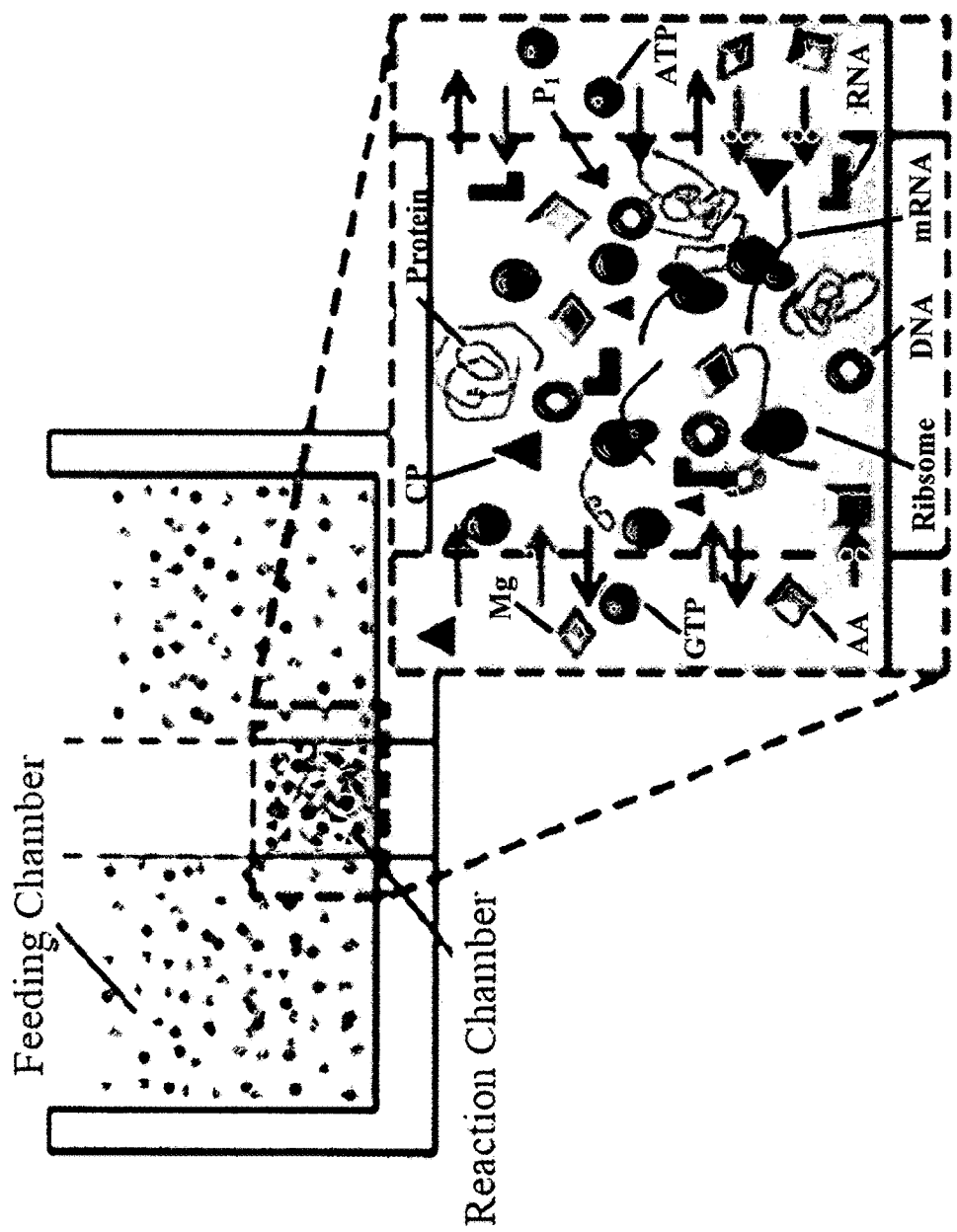

A μFAD in the CECF format was developed to enable the high-throughput selection and optimization of the components of the feeding solution for the PURE system. The device layout is shown in FIG. 14*a*. The device is in the 96-unit format, compatible with standard 96-well microplate readers and reagent dispensers. Each protein expression unit consists of three chambers, with the central reaction chamber separated from the two feeding chambers by dialysis membranes that are oriented vertically to the table surface. During protein expression, the nutrient and energy molecules move from the feeding solution into the reaction solution to replenish the reactants and support protein expression while the inhibitory byproducts produced in the reaction chamber simultaneously diffuse across the dialysis membranes into the feeding chambers as depicted in FIG. 14*b*.

The reaction and feeding chambers with a depth of about 5 mm were milled into about 6.35 mm thick polycarbonate sheets (McMaster-Carr, Atlanta, Ga., USA), and 6-8 kDa molecular weight cutoff dialysis membranes (Spectrum Labs, Rancho Dominguez, Calif., USA) were cut to the size using a plotting cutter (Craft ROBO Pro, Graphtec, Irvine, Calif., USA). The dialysis membranes and polycarbonate pieces were then bonded together using polydimethylsiloxane (PDMS) (Sylgard 184, Dow Corning) by a microstamping technique. This microstamping technique involved preparing a PDMS solution according to the manufacturer's instructions and spinning a thin layer of PDMS onto a plastic sheet using a spinner (Laurell Technologies) at 1500 revolutions per minute (RPM) for 15 s. A thin layer of PDMS was then transferred onto the surfaces of a polycarbonate piece by stamping the piece on the plastic sheet. The polycarbonate pieces and dialysis membranes were then assembled and secured together using a clamping frame and placed in an oven at 70° C. for four hours and kept at room temperature overnight. The assembled device was then removed from the frame and placed in a 96-well holder for experiments.

Plasmid Construction

Plasmids used for CFPS experiments contained a T7 promoter upstream of the Shine-Dalgarno sequence. The GFP vector was obtained from the RTS 100 HY E. coli Kit (5Prime, Gaithersburg, Md., USA). The E. coli gene for LacZ was cloned into vector pUC18 (Takara Bio, Japan).

PURE System Preparation

The components necessary for protein synthesis except for the GFP vector were provided by and prepared at the University of Tokyo as previously described (Shimizu et al. (2001), Shimizu et al. (2005) and Shimizu et al. (2010)). In short, ribosomes from E. coli A19 cells were purified by hydrophobic chromatography by Ohashi et al. (2007). For the CFPS protein factors, the E. coli genes for aminoacyl-tRNA synthetases (ARSs), methionyl-tRNA transformylase (MTF), nucleoside-diphosphate kinase, initiation factors (IF1, IF2, IF3), elongation factors (EF-G, EF-Tu, EF-Ts), release factors (RF1, RF2, RF3), and ribosome-recycling factor (RRF) were amplified and cloned into His-tag vectors, and the resulting plasmids were transformed into E. coli BL21 cells. After the cells were grown, collected, resuspended, and lysed, the supernatant was added to a $Ni^{2+}$ precharged Hi-Trap chelating column (Amersham Pharmacia, Biotech, Arlington Heights, Ill., USA) and washed with an HT buffer (50 mM Hepes-KOH, pH 7.6, 100 mM potassium chloride, 10 mM magnesium chloride, 500 mM imidazole, pH 7.6, 7 mM 2-mercaptoethanol) to elute the His-tag proteins. Similarly, other enzymes, including T7 RNA polymerase, myokinase, creatine kinase, and pyrophosphatase, were also overexpressed in E. coli with His-tag and purified as described above.

Protein Expression

The reaction solution was prepared according to the previously published reagent concentrations (Shimizu et al. (2005)) with 2.7 µM IF1, 0.40 µM IF2, 1.5 µM IF3, 0.26 µM EF-G, 0.92 µM EF-Tu, 0.66 µM EF-Ts, 0.25 µM RF1, 0.24 µM RF2, 0.17 µM RF3, 0.50 µM RRF, 1900 U/ml AlaRS, 2500 U/ml ArgRS, 20 mg/ml AsnRs, 2500 U/ml AspRs, 630 U/ml CysRs, 1300 U/ml GlnRs, 1900 U/ml GluRs, 5000 U/ml GlyRs, 630 U/ml HisRs, 2500 U/ml IleRS, 3800 U/ml LeuRS, 3800 U/ml LysRS, 6300 U/ml MetRS, 1300 U/ml of PheRS, 1300 U/ml ProRS, 1900 U/ml SerRS, 1300 U/ml ThrRS, 630 U/ml TrpRS, 630 U/ml TyrRS, 3100 U/ml ValRS, 4500 U/ml MTF, 1.2 µM ribosomes, 4.0 µg/ml creatine kinase, 3.0 µg/ml myokinase, 1.1 µg/ml nucleoside-diphosphate kinase, 2.0 units/ml pyrophosphatase, 10 µg/ml T7 RNA polymerase, 2 mM ATP, 2 mM GTP, 1 mM CTP, 1 mM UTP, 20 mM creatine phosphate, 50 mM Hepes-KOH (pH 7.6), 100 mM potassium glutamate, 13 mM magnesium acetate, 2 mM spermidine, 1 mM dithiothreitol (DTT), 0.3 mM 20 amino acids, 10 µg/ml 10-formyl-5,6,7,8-tetrahydrofolic acid, and 56 $A_{260}$/ml tRNA mix. They are outlined in Table 1. The added DNA vector had a final concentration of 10 ng/µl. The feeding solution, unless otherwise specified, consists of 2 mM ATP, 2 mM GTP, 1 mM CTP, 1 mM UTP, 20 mM creatine phosphate, 50 mM Hepes-KOH (pH 7.6), 100 mM potassium glutamate, 13 mM magnesium acetate, 2 mM spermidine, 1 mM DTT, 0.3 mM 20 amino acids, and 10 µg/ml 10-formyl-5,6,7,8-tetrahydrofolic acid, as outlined in Table 2.

TABLE 1

Reagent components and concentrations for the initial and optimized feeding solutions.

| Initial Feeding Solution | Optimized Feeding Solution |
|---|---|
| Buffer Components | Buffer Components |
| 50 mM HEPES-KOH (pH 7.6) | 50 mM HEPES-KOH (pH 7.6) |
| 100 mM Potassium Glutamate | 100 mM Potassium Glutamate |
| 13 mM Magnesium Acetate | 17 mM Magnesium Acetate |
| 2 mM Spermidine | 2 mM Spermidine |
| 1 mM DTT | 1 mM DTT |
| Energy and Nutrient Molecules | Energy and Nutrient Molecules |
| 2 mM ATP | 4 mM ATP |
| 2 mM GTP | 4 mM GTP |
| 1 mM CTP | 1 mM CTP |
| 1 mM UTP | 1 mM UTP |
| 20 mM Creatine Phosphate | 20 mM Creatine Phosphate |
| 0.3 mM Amino Acids | 0.5 mM Amino Acids |
| 10 µg/ml 10-Formyl-5,6,7,8-Tetrahydrofolic Acid | 10 µg/ml 10-Formyl-5,6,7,8-Tetrahydrofolic Acid |

TABLE 2

Reagent components and concentrations for the reaction solution.

| Initiation, Elongation and Release Factors |
|---|
| 2.7 µM IF1 |
| 0.40 µM IF2 |
| 1.5 µM IF3 |
| 0.26 µM EF-G |
| 0.92 µM EF-Tu |
| 0.66 µM EF-Ts |
| 0.25 µM RF1 |
| 0.24 µM RF2 |
| 0.17 µM RF3 |
| 0.50 µM RRF |
| Enzymes |
| 4500 U/ml MTF |
| 1.2 µM Ribosomes |
| 4.0 µg/ml Creatine Kinase |
| 3.0 µg/ml Myokinase |
| 1.1 µg/ml Nucleoside-Diphosphate Kinase |
| 2.0 units/ml Pyrophosphatase |
| 10 µg/ml T7 RNA Polymerase |
| Energy and Nutrient Molecules |
| 2 mM ATP |
| 2 mM GTP |
| 1 mM CTP |
| 1 mM UTP |
| 20 mM Creatine Phosphate |
| 0.3 mM Amino Acids |
| 10 µg/ml 10-Formyl-5,6,7,8-Tetrahydrofolic Acid |
| Aminoacyl-tRNA Synthetases and tRNA |
| 1900 U/ml AlaRS |
| 2500 U/ml ArgRS |

TABLE 2-continued

Reagent components and concentrations for the reaction solution.

20 mg/ml AsnRS
2500 U/ml AspRS
630 U/ml CysRS
1300 U/ml GlnRS
1900 U/ml GluRS
5000 U/ml GlyRS
630 U/ml HisRS
2500 U/ml IleRS
3800 U/ml LeuRS
3800 U/ml LysRS
6300 U/ml MetRS
1300 U/ml PheRS
1300 U/ml ProRS
1900 U/ml SerRS
1300 U/ml ThrRS
630 U/ml TrpRS
630 U/ml TyrRS
3100 U/ml ValRS
56 $A_{260}$/ml tRNA Mix
Buffer Components 50 mM HEPES-KOH (pH 7.6)
100 mM Potassium Glutamate
13 mM Magnesium Acetate
2 mM Spermidine
1 mM DTT Experiments in the batch format were carried out by pipetting 10 μl of the reaction solution into a well of a conventional 96-well microplate. For the continuous-exchange cell-free (CECF) format in the μFAD device, 10 μl of the reaction solution is dispensed into the reaction chamber while a total of 200 μl of the feeding solution was pipetted into the feeding chambers (100 μl in each of two feeding chambers). Negative controls were prepared by replacing the DNA in the reaction solution with an equal volume of nuclease-free water for both the batch and CECF formats. To prevent evaporation, the conventional microplate and μFAD were covered with a PCR tape and left at room temperature (27° C.) for 4 hours for protein expression unless otherwise specified.

For feeding solution optimization, the concentrations of creatine phosphate, ATP, GTP, magnesium acetate, and the 20 amino acids were systematically varied from 10 to 50 mM, 1 to 5 mM, 1 to 5 mM, 13 to 23 mM, and 0.1 to 1 mM, respectively, to determine the optimal reagent concentrations for maximum protein expression. GFP was expressed in all optimization experiments.

GFP Productivity Quantification

Figure 13:
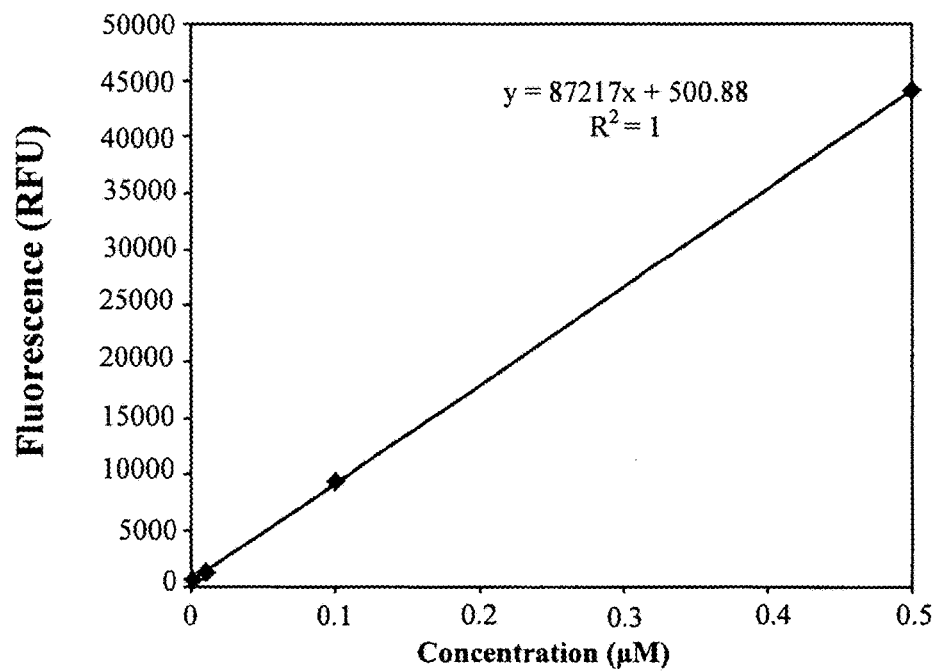
FIG. 13. Calibration curve and trendline for purified recombinant GFP (rGFP). The concentration of rGFP was varied from 1 nM to 0.5 μM, and the resulting fluorescence signal was measured. A simple linear regression was then performed to determine the equation of the trendline and coefficient of determination ($R^2$ value) for the resulting data.

A calibration curve for rGFP (Takara Bio Inc., Shiga, Japan) (FIG. 13) was established by varying the concentration of rGFP from 1 nM to 0.5 μM and measuring the resulting fluorescent signal. The resulting linear regression line and equation were used to determine the concentration of expressed GFP for the batch and CECF formats with the initial and optimized feeding solutions.

Product Analysis

For quantification of expressed GFP and LacZ, the produced fluorescence signal was measured for 10 s using a microplate reader (1420 Multilabel Counter, Wallac ARVO SX, Amersham Biosciences Corp., Piscataway, N.J., USA) with excitation and emission wavelengths of 485 and 535 nm, respectively. For expressed LacZ, it also required the addition of 30 μl of 200 μM fluorescein mono-β-D-galactopyranoside (FMGal) (MarkerGene Technologies, Eugene, Oreg., USA) and 15 minutes of incubation prior to fluorescence measurement. Reported results were obtained by subtracting the background fluorescence (the negative control) from the measured fluorescent signal in both batch and CECF formats. Each experiment was repeated three times, and the results from each experiment were normalized against the measured fluorescent signal from protein expression with the initial feeding solution. A p-value less than 0.01 was considered statistically significant.

EXAMPLE 1

Apparatuses for High Throughput Protein Synthesis

With the completion of the Human Genome Project in 2003 and the vast number of genes identified, understanding the structural and functional properties of the proteins encoded in these genes has become an important area of research in proteomics. Synthesizing proteins necessary for these studies would typically involve cellular expression systems using primarily *E. coli*.[1-4] However, such cellular expression systems have several limitations, including the formation of inclusion bodies, protein degradation through proteolysis, lack of post-translational modification, and inability to synthesize cytotoxic proteins. Cellular expression systems have been expanded to include eukaryotic cells to combat these limitations, but expression of cytotoxic proteins and proteolysis still present problems.[1-4]

An alternative to protein expression in intact cells is cell-free protein synthesis (CFPS), which involves using the lysate from a cellular system for protein synthesis. CFPS requires the following components: a genetic template (e.g., DNA) with the target gene, the machinery necessary for transcription and translation (e.g., ribosomes), and a solution containing energy molecules such as adenosine-5'-triphosphate (ATP) and nutrients (e.g., amino acids) necessary to sustain protein expression. Compared to traditional protein expression within an intact cell, CFPS reduces protein synthesis time, eliminates cytotoxicity concerns, reduces proteolysis, and allows greater control over the chemicals included for protein synthesis.[5,6] These advantages have enabled CFPS applications to be expanded to structural and functional proteomics,[7-9] synthesis and characterization of cytotoxic proteins,[10-11] drug discovery and screening,[12-13] and high-throughput protein synthesis.[14-16]

CFPS has been performed in three formats. The first one is a simple batch format characterized by low protein synthesis yields and long processing times as a result of the depletion of energy/nutrients and the accumulation of inhibitory byproducts.[5-6] To eliminate these disadvantages, Spirin and co-workers developed the continuous-flow format, in which a feeding solution containing energy/nutrient molecules is continuously supplied and the inhibitory byproducts are removed through filtration membranes.[6,17] Although studies with alternate designs and chemical compositions of the continuous-flow CFPS system have been carried out, membrane clogging and leakage limit the maximum protein synthesis time and yield possible within the systems.[6,18] The third format, continuous-exchange CFPS is similar to the continuous-flow format with the continuous supply of nutrients and removal of byproducts. However, this exchange of small molecules between the reaction solution and the feeding solution occurs passively through the membrane, and the protein synthesis yield is generally greater.[18-20]

Recently, miniaturized CFPS in the continuous-exchange format have been studied in order to achieve high throughput, reduce reagent consumption, and speed up protein synthesis. These goals have been accomplished in the form of droplets,[21-24] protein-producing gel,[25] and microfluidic devices.[14,26-28] With the droplets, a pseudo-filtration membrane is formed through oil-in-water emulsions; and the platform offers a ultrahigh-throughput screening method since a large number of droplets can be easily and rapidly created.[21-24] For the protein-producing gel, the isolation of the genetic template and reaction solution is achieved through a hydrogel, and the large surface-area-to-volume ratio of the reaction vessel enhances protein synthesis yield.[25] In microfluidic devices, either a nanoporous membrane or a liquid lipid membrane is used to separate the reaction solution from the feeding solution to allow continuous exchange of certain chemicals. By scaling the devices for additional protein expression units, high-throughput protein synthesis is possible.[14,26-28]

We have provided a miniaturized array of apparatuses for continuous-exchange CFPS, and investigated the effect of membrane orientation on protein synthesis yield. Compared to the devices reported previously[14] the porous membrane in this invention is oriented vertically in reference to the table surface to reduce or eliminate possible membrane clogging (due to possible sedimentation of large molecules such as aggregated proteins or ribosomes). The apparatuses of the current invention can be further optimized by studying the effects of hydrostatic pressure and reaction times on protein synthesis yield.

The protein synthesis yield in these devices was compared with the previous devices with membranes oriented horizontally[14] as well as with a conventional multi-well micro-plate. The difference in the protein synthesis yield due to membrane clogging was confirmed by dye passage experiments. The devices have been designed to be compatible with a micro-plate reader to allow high-throughput protein synthesis and drug screening.

Results and Discussion

Membrane Orientation. In a device for continuous exchange CFPS, the porous membrane serves to segregate the reaction solution from the feeding solution while simultaneously allowing for the exchange of vital molecules between the two solutions. This separation isolates all of the machinery necessary for DNA transcription and protein translation within the reaction chamber, creating a highly concentrated environment for protein synthesis. As proteins are synthesized, energy and nutrients within the reaction chamber are depleted and byproducts such as inorganic phosphate are accumulated. Without the porous membrane, these two conditions would hinder further protein synthesis. With the porous membrane, however, small nutrient/energy molecules from the feeding solution can pass into the reaction solution and the byproducts can diffuse from the reaction solution to the feeding solution, thus sustaining protein synthesis.

The porous membranes can be oriented either horizontally or vertically within the device. In the horizontal orientation as in FIG. 1B, heavy molecules such as protein aggregates or ribosome may settle down on the membrane, potentially blocking the membrane pores and thus hampering protein synthesis. By orienting the membranes vertically as in FIG. 1C, large molecules would settle against the polycarbonate surface at the bottom of the device, eliminating membrane blockage and increasing protein synthesis.

To determine if membrane orientation impacts protein expression, Vertical Apparatus I (FIG. 1D) was designed and fabricated based on the previously reported[14] Horizontal Apparatus (FIG. 1A). As conveyed by FIGS. 1B and 1C, Vertical Apparatus I has a single feeding chamber and a reaction chamber surrounded by access wells to the feeding chamber. However, Vertical Apparatus I consists of five layers instead of three. The two additional layers (the access layer and valve membrane), as well as the passage region in the reaction chamber layer, prevent leakage of fluid out of the device when the device is placed vertically during protein synthesis.

Table 3 illustrates the effect of membrane orientation on GUS synthesis yield. Fluorescence measurement is used to quantify the amount of GUS expressed in various devices. The negative control is the replacement of the GUS vector with nuclease-free water in Vertical Apparatus I. In the conventional micro-plate, the observed protein expression is the result of the minimal amount of nutrients and energy included in the reaction solution used. By including a porous membrane for the replenishment of nutrients and removal of byproducts, GUS synthesis yield increased 67-fold in the Horizontal Apparatus. The synthesis yield of GUS further increased to 174-fold in Vertical Apparatus I. In other words, an increase of 2.6-fold in GUS synthesis yield was obtained by orienting the porous membrane vertically.

TABLE 3

Comparison of protein synthesis yields in various apparatuses.

| | Fluorescence Signal (RFU × $10^5$) | Synthesis Yield fold Increase* |
|---|---|---|
| Vertical-I | $(2.26 \pm 0.20) \times 10^3$ | 174 |
| Horizontal device | $(8.7 \pm 1.6) \times 10^2$ | 67 |
| Conventional micro-plate | $(1.30 \pm 0.27) \times 10^1$ | 1 |
| Negative control | $5.33 \pm 0.03$ | N/A |

Note:
*The synthesis yields of GUS in Vertical-I and Horizontal Device were normalized against that in a conventional micro-plate.

Since Vertical Apparatus I was designed to compare the effects of device orientation, fabrication and use of Vertical Apparatus I are often a challenge. The device is oriented horizontally when the solutions are dispensed into the chambers, and it must be carefully rotated to be vertically oriented before the reactions take place. When dispensing the reaction solution, the pipette should touch the porous membrane so that the solution does not remain on the plastic wall (due to surface tension). At the same time, caution must be exercised to avoid accidental piercing of the membrane. Also, by depositing directly onto the porous membrane, most of the reaction solution will remain in contact with the porous membrane as a result of surface tension, and they will flow to the bottom of the reaction chamber as a result of gravity after the device rotation.

To avoid these problems, Vertical Apparatus II (FIG. 2) was designed and fabricated. This device has a central reaction chamber with two feeding solution interfaces to provide maximal contact between the reaction and feeding solutions. The device design also allows for expedient deposition of solutions without the necessity of puncturing porous membranes. For experiments, the ratio of reaction solution to feeding solution remained 20:1 with 100 μL of feeding solution pipetted into each feeding chamber.

Since optimization is device dependent, both vertically oriented devices were studied with geometry variation and other conditions as discussed below. Comparison between devices was made, and the effects of the vertical orientation of the porous membrane on the reaction kinetics were studied.

Hydrostatic Pressure. The chemical exchange between the reaction and feeding solutions occurs as a result of concentration gradients and the subsequent passage of solutes in the solutions. To determine if hydrostatic pressure caused by height differences between the feeding and reaction solutions contributed to this exchange in the vertically oriented devices, the height of the reaction chamber was varied in Vertical Apparatus II, and the hydrostatic pressure was characterized by the height difference ($\Delta h$) between the feeding and reaction solutions. A positive height difference is indicative of a feeding solution level greater than the reaction solution, which corresponds to the movement of solution from the feeding chamber into the reaction chamber. A negative height difference indicates that the feeding solution level is below the reaction solution level and the flow of reaction solution from the reaction chamber to the feeding chamber. A height difference of 0 mm corresponds to equal solution heights, and the flow of solutes between the chambers is attributed to passage only. This experiment was not performed in Vertical Apparatus I as the height difference between the solutions is difficult to be determined due to partial wetting of the membrane when dispensing solutions.

Figure 3:
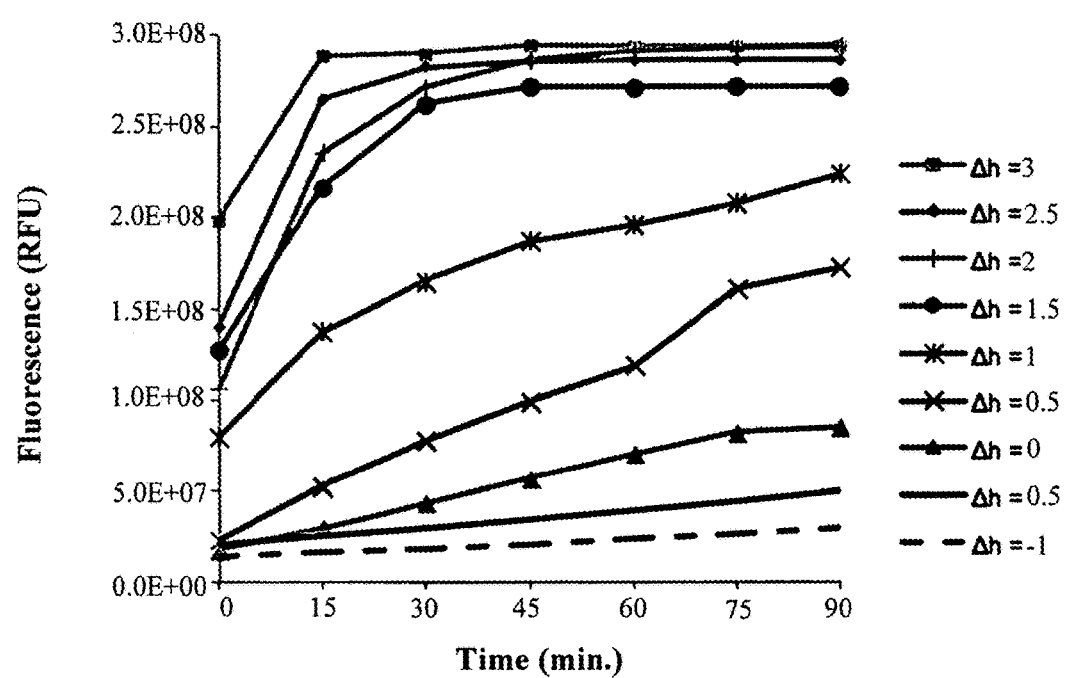
FIG. 3. The effect of hydrostatic pressure on protein synthesis in Vertical Apparatus II. The Δh value was the height difference between feeding and reaction solutions and varied between −1 and 3 mm. Devices were fabricated by varying the reaction chamber depth and feeding chamber width. Each data point represents the average of the results from three experiments.

As shown in FIG. 3, hydrostatic pressure effects are present in the system as the measured fluorescence signal increases with an increase in the height difference between the solutions. This trend is in general agreement with the hydrostatic pressure effects previously observed in the Horizontal Apparatus.[19] The greatest protein expression occurs when the height difference between the feeding and reaction solutions is greater than 2 mm. At this height difference, hydrostatic pressure increases the influx of feeding solution into the reaction chamber, supplementing the reaction solution with a greater amount of nutrients and energy for protein expression. For later experiments, the height difference of 3 mm was chosen since this height difference happens to have equal reaction and feeding chamber depths for the geometry we chose for Vertical Apparatus II.

Reaction Time. The time allotted for molecule exchange and protein expression also impacts protein synthesis yield since the yield is dependent on both DNA template concentration and experimental timing.[30] Protein expression increases with reaction time until the depletion of nutrients and accumulation of byproducts sufficiently slow down reactions. With the porous membranes in continuous-exchange CFPS systems, reaction termination is delayed as a result of the controlled exchange of solutes across the porous membrane. As a result, protein synthesis yields are greater than batch systems such as in the conventional micro-plate.

Figure 4:
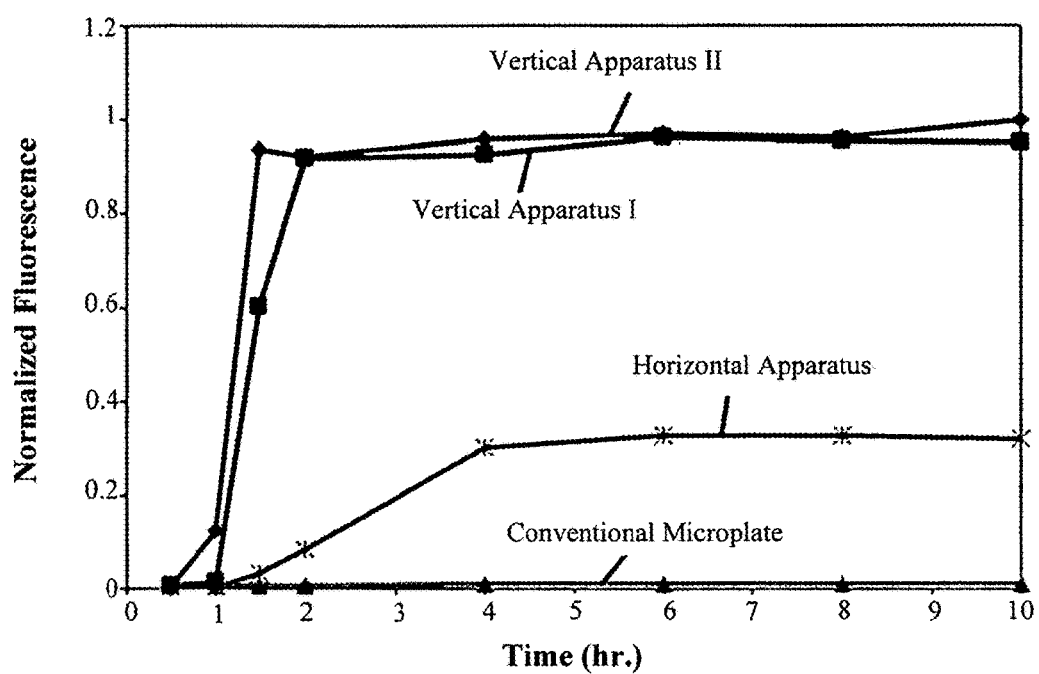
FIG. 4. The effect of reaction time on protein synthesis in four types of CFPS devices. Protein expression in each device was permitted for 0.5, 1, 1.5, 2, 4, 6, 8, and 10 hours. The protein synthesis yield as quantified by the fluorescence signal is normalized against the highest fluorescent signal.

To monitor the reaction time for protein synthesis in the vertically oriented devices, protein synthesis was allowed to occur for 0.5, 1, 1.5, 2, 4, 6, 8, and 10 hours before adding the assay reagent (MUG) and measuring the fluorescence signal. The same experiment was conducted in the conventional micro-plate and Horizontal Apparatus for comparison, and the results are shown in FIG. 4. Protein synthesis yield reached to plateau after 1.5 hours in Vertical Apparatus II and 2 hours in Vertical Apparatus I. For the Horizontal Apparatus, protein synthesis yield plateaued after 4 hours of reactions. The difference in the reaction times between vertically and horizontally oriented devices is likely attributed to the sedimentation of large molecules (e.g., ribosomes or aggregated proteins) in the reaction solution. With the vertically oriented devices, large molecules may settle at the bottom of the device instead of against the porous membrane, allowing molecule exchange to occur efficiently and expediently. In the Horizontal Apparatus, sedimentation likely blocks pores, hindering molecule exchange and prolonging reaction termination.

Reaction Temperature. CFPS can be carried out at a temperature of about 20° C. to about 45° C., about 25° C. to about 40° C., about 30° C. to about 37° C. Specifically, CFPS can be carried out at room temperature or a temperature of about 37° C.

Passage Measurement. To determine if possible settling of large molecules is occurring in the Horizontal Apparatus and alleviated when the porous membrane is oriented vertically, we performed experiments to monitor the passage of fluorescein in the Horizontal Apparatus, Vertical Apparatus I, and Vertical Apparatus II. For monitoring movement of the chemicals from the reaction solution to the feeding solution, the first setup was to add fluorescein in the reaction solution, followed by the measurement. For the chemical movement from the feeding solution to the reaction solution, the second setup with the addition of fluorescein to the feeding solution was used. The results from the first and second setup are depicted in FIGS. 5A and 5B.

The results illustrate the greatest chemical movement from both the reaction and feeding solutions in Vertical Apparatus II, followed by Vertical Apparatus I and the Horizontal Apparatus. The lowest fluorescence in the Horizontal Apparatus indicates the slowest passage through the porous membrane, suggesting possible sedimentation of large molecules onto the membrane. Higher fluorescence in the vertically oriented devices suggests the reduction or elimination of such effects. These results explain that the orientation of Vertical Apparatus I and Vertical Apparatus II resulted in higher protein synthesis yield.

Figure 5:
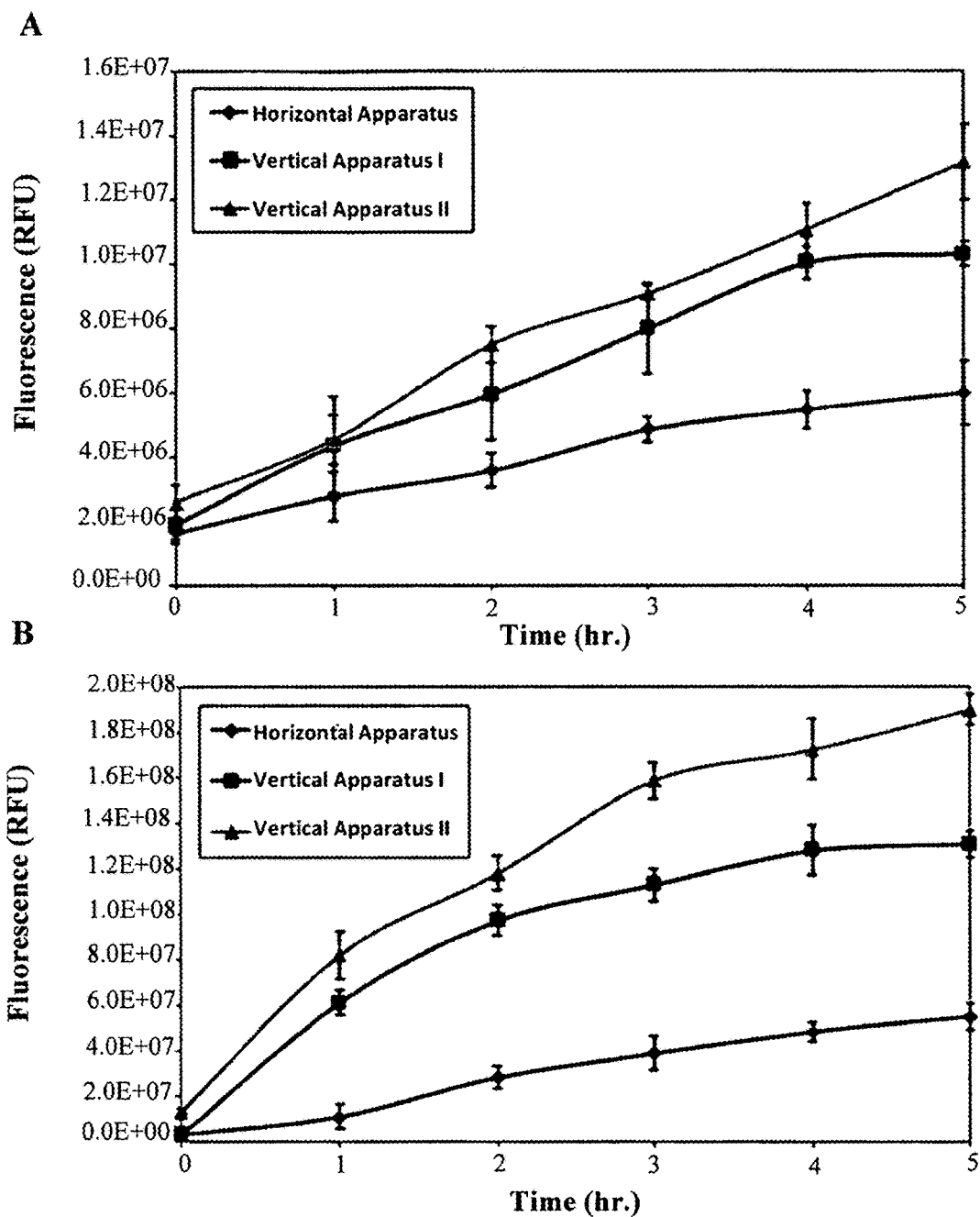
FIGS. 5A-5B. A. Passage of fluorescein from the reaction chamber across the dialysis membrane to the feeding chamber for the Horizontal Apparatus, Vertical Apparatus I, and Vertical Apparatus II. B. Passage of fluorescein from the feeding chamber across the dialysis membrane to the reaction chamber for these devices.
Figure 6:
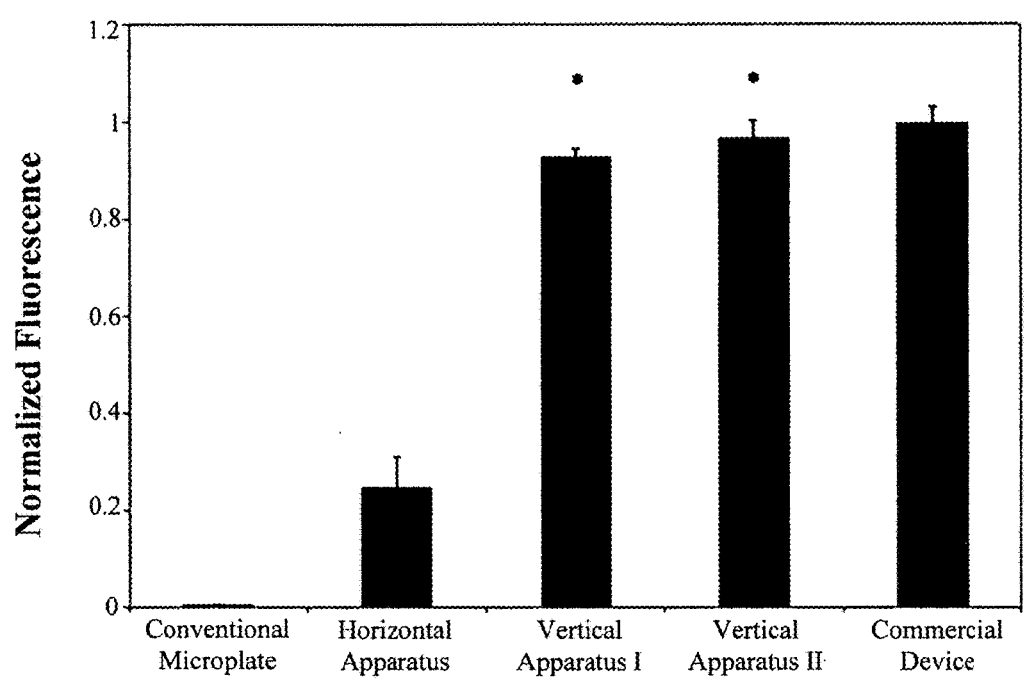
FIG. 6. Comparison in GUS synthesis yields among the conventional micro-plate, Horizontal Apparatus, Vertical Apparatus I, Vertical Apparatus II, and RTS100. The protein synthesis yield was quantified by the fluorescence signal after adding the assay reagent (MUG). The signals were normalized against the highest signal. The average of three repeated experiments is plotted and the error bars indicate one standard deviation. Asterisk (*) indicate a p-value less than 0.05 between two sets of data.

Difference between FIGS. 5A and 5B is likely contributed by the hydrodynamic pressure as discussed above. The feeding solution level was 3 mm higher than the reaction solution level in both cases, thus we expect more passage of fluorescein from the feeding chamber to the reaction chamber in FIG. 5B.

Figure 12:
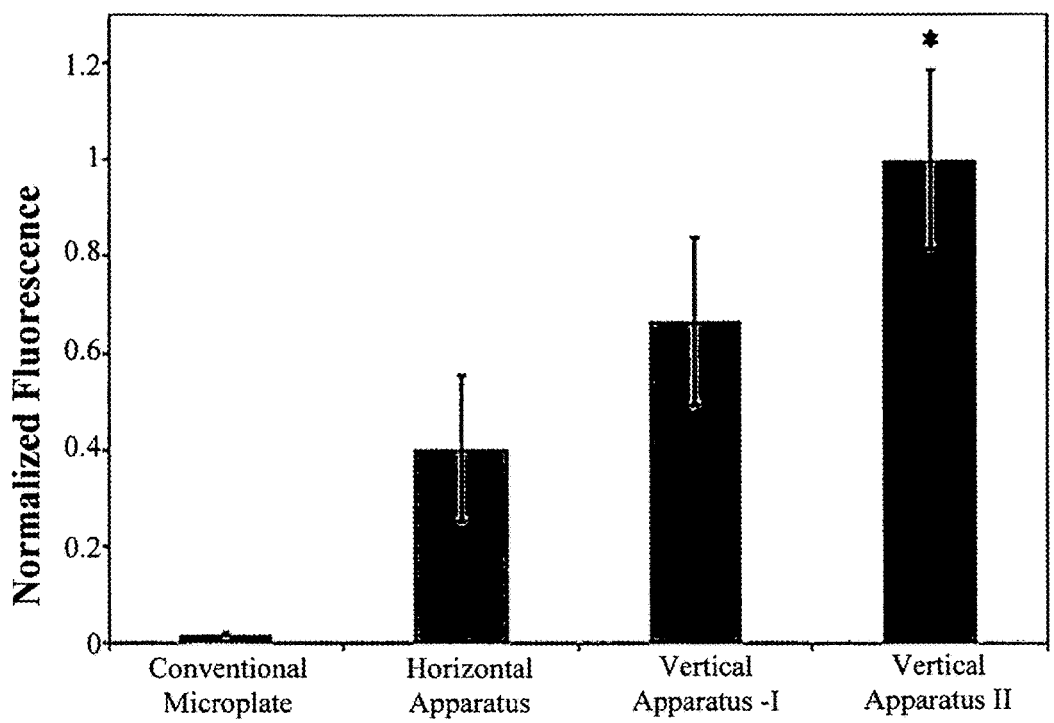
FIG. 12. Comparison in luciferase synthesis yield among the conventional microplate, Horizontal Device, Vertical apparatus-I, and Vertical apparatus-II. The protein synthesis yield was quantified by the luminescence signal after adding the luciferase assay reagent (LAR). The signals were normalized against the highest signal and they represented the measured luminescence per unit interface area between the feeding and reaction solutions. The average of three repeated experiments is plotted and the error bars indicate one standard deviation. Star (*) indicates a p-value of less than 0.05 between the horizontal apparatus and the Vertical Apparatus II.

Protein Synthesis. After device geometry optimization and reaction time studies, GUS expression was performed in the conventional micro-plate, Horizontal Apparatus, Vertical Apparatus I, and Vertical Apparatus II, and the results are compared in FIG. 19. Luciferase was also expressed in the conventional microplate, Horizontal Device, Vertical-I, and Vertical-II, and the results are depicted in FIG. 12. The expression yields in both figures were normalized per unit interaction area between the feeding and reaction solutions. The interaction areas between the two solutions were ~15.9 $mm^2$ for the Horizontal Device and Vertical-1 and 8 $mm^2$ for Vertical-II. For this experiment, the reaction time was 4 hours for each device to account for the delayed plateau period in the Horizontal Apparatus. The results from this experiment show that GUS expression is highest in Vertical Apparatus II. Compared to the Horizontal Apparatus, an increase of 144% and 406% in GUS expression per unit volume and interaction area between the feeding and reaction solutions is observed in Vertical Apparatus I and Vertical Apparatus II, respectively. The results show that possible sedimentation of large molecules onto horizontal porous membranes negatively affects the protein synthesis. By orienting these membranes vertically, the issue is eliminated or reduced and GUS synthesis yield is substantially increased. Although Vertical Apparatus II was designed to ease fabrication issues with Vertical Apparatus I and for the compatibility with a conventional micro-plate holder, the optimized Vertical Apparatus II has an a statistically significant increase ($p \leq 0.05$) of 107% in GUS synthesis yield over the optimized Vertical Apparatus I.

Figure 19:
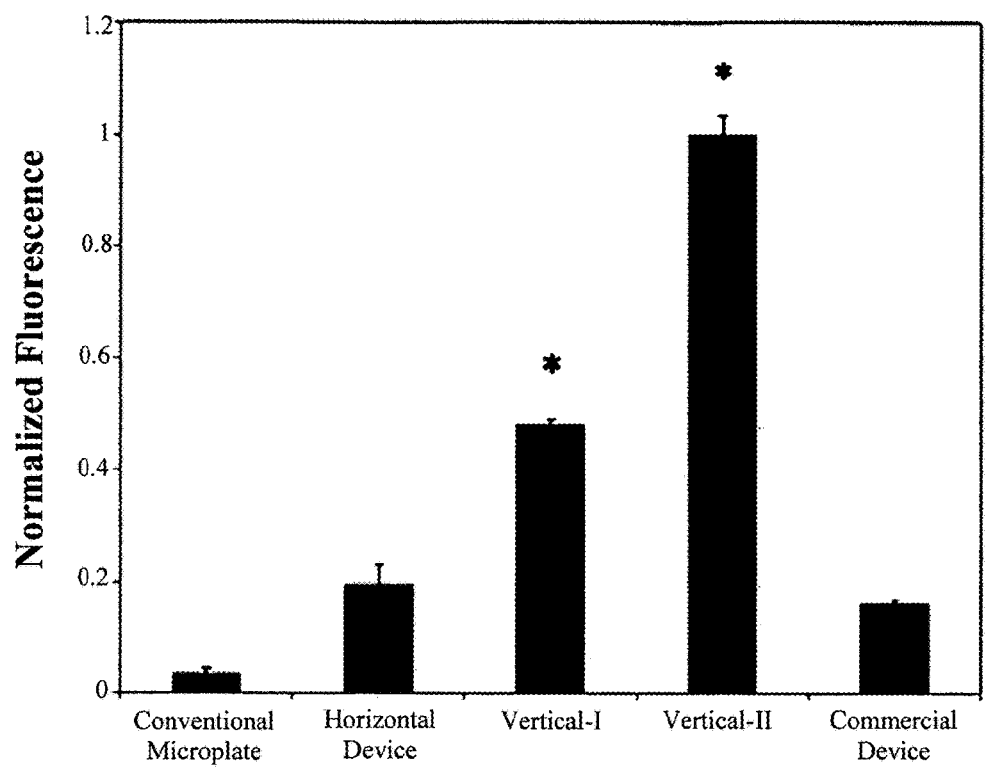
FIG. 19. Comparison in β-glucuronidase (GUS) synthesis yield among the conventional microplate, Horizontal Device, Vertical-I, Vertical-II, and commercial RTS100 device. The protein synthesis yield was quantified by the fluorescence signal after adding the assay reagent (4-methylumbelliferyl-β-D-glucuronide). The signals were normalized against the highest signal, and they represent the fluorescence per unit volume and unit interface area between the feeding and reaction chambers. The average of three repeated experiments is plotted, and the error bars indicate one standard deviation. The stars (*) indicate a p value less than 0.05 in a comparison between Vertical-I and Vertical-II with the Horizontal Device.

The commercially available RTS100 kit that includes a CECF device with two compartments, one for the reaction and the other for feeding solutions, was compared with the apparatuses of the current invention. In RTS100, a semipermeable membrane is horizontally oriented. Compared to the apparatuses of the current invention, the RTS100 system requires five times as much solution as in our devices since the manufacturer's instructions specifies 50 μL of the reaction solution and 1 ml of the feeding solution. To accommodate more reaction solution volume in the commercial device, 150 μL of MUG was used to ensure sufficient assay reagents (compared to using 30 μL for our devices). Also, the membrane area in RTS100 is about ~50 mm$^2$ while the membrane contact area in Vertical Apparatus II is 8 mm$^2$. A larger membrane contact area leads to more efficient exchange and thus higher protein synthesis yield. Considering the differences in both volume and the membrane area, Vertical Apparatus II generated protein synthesis yield 505% over RTS100 as shown in FIG. 19. A probability test comparing Vertical-II with the commercial device indicates that there is a statistical difference in protein synthesis yield with a P value less than 0.05, indicating they are statistically different at 95% confidence level. These results demonstrate the advantages of the apparatuses of the current invention in terms of reducing the reagent consumption and protein synthesis efficiency.

Vertical Apparatuses I and II of the current invention demonstrate the effect of membrane orientation on protein synthesis yield. With the vertical orientation of the membrane, nanopore clogging is reduced or eliminated because the large molecules settle down to the bottom of the device instead of the porous membrane, thus improving protein synthesis yield.

The vertically oriented apparatuses were experimentally optimized by studying the effects of hydrostatic pressure and reaction time on protein expression. These studies indicate that hydrostatic pressure had an impact on protein expression, and the greatest protein synthesis yield occurred when the height difference between the reaction and feeding solutions was maximized. The reaction time for the vertically oriented devices was found to be less than the horizontally oriented device. With membrane clogging reduced in the vertically oriented devices, chemical exchange across the porous membrane occurred more efficiently and expediently.

Vertical Apparatuses I and II demonstrate that protein synthesis yield in the vertically oriented apparatuses is significantly enhanced compared to the horizontal apparatuses. Protein expression per unit volume and interaction area between the feeding and reaction solutions in Vertical Apparatus I and Vertical Apparatus II increased by 144% and 406%, respectively, and the vertically oriented apparatuses produce protein synthesis yields 505% over the commercial RTS100 device. However, due to their smaller sizes the apparatuses of the current invention require five times less reagents than RTS100 device. The judicious design enabled Vertical-II to be compatible with a conventional 96-well microplate while using five times less reagents than the commercial RTS100 device. With this compatibility for commercial reagent dispensers and micro-plate readers, as well as rapid reactions and high synthesis yields, Vertical Apparatuses I and II have applications in high-throughput protein synthesis and drug screening.

EXAMPLE 2

The Single-Sided Vertical Apparatus

Figure 7:
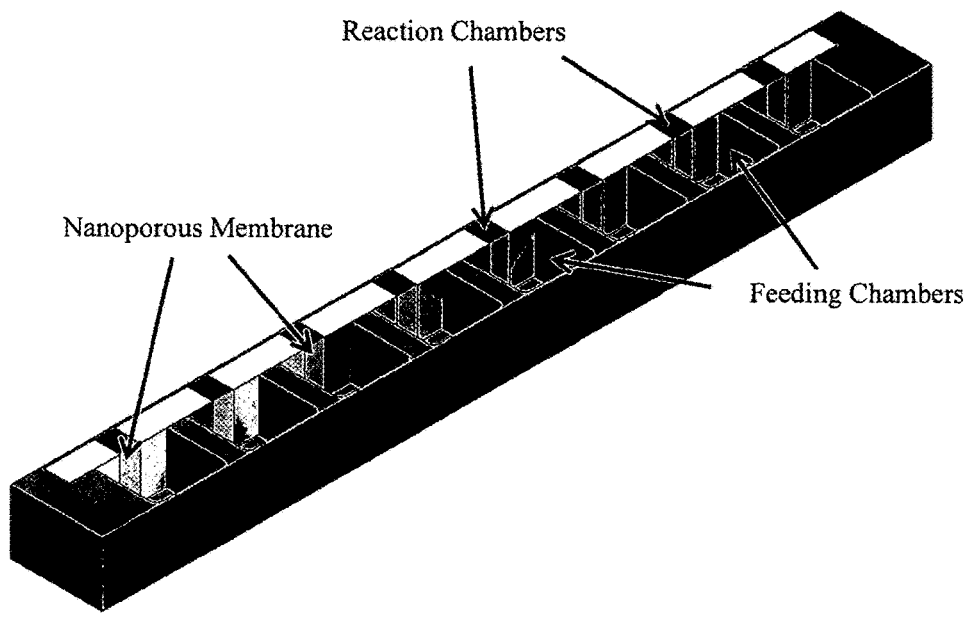
FIG. 7. 3-D rendering of the single-sided vertical apparatus with the reaction chambers, feeding chambers, and nanoporous membrane identified.

In the apparatus referred to as the single-sided vertical the reaction solution is separated from the feeding solution by a single nanoporous membrane as shown in FIG. 7. As a result, the reaction chamber section is sandwiched between a solid wall and the membrane, and the two feeding chambers in Vertical Apparatus II are combined to make a larger feeding chamber.

EXAMPLE 3

The Channel Apparatus

Figure 8:
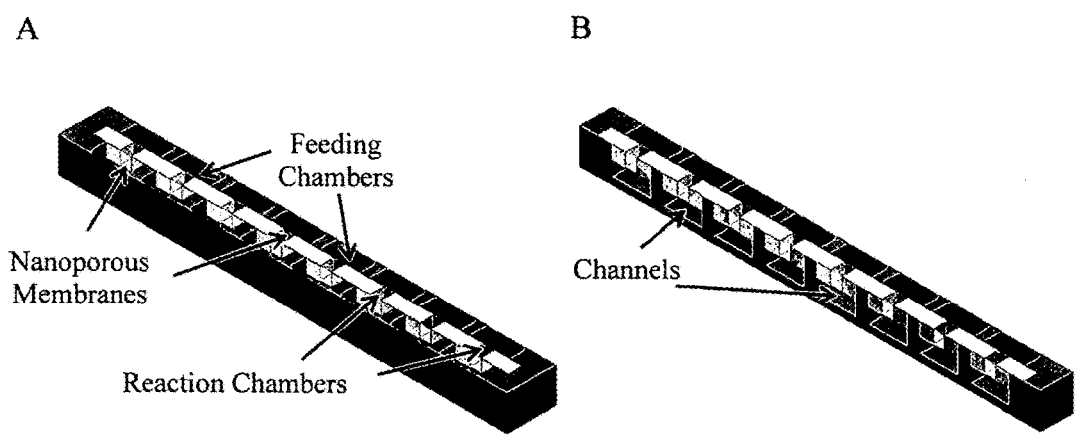
FIGS. 8A-8B. 3-D renderings of the channel apparatus. A. An illustration of the entire apparatus with the reaction chambers, feeding chambers, and nanoporous membranes identified. B. Cross-sectional view of the apparatus with the channels identified.

In this apparatus, a channel connecting the two feeding chambers beneath the reaction chamber is provided. The reaction solution is separated from the feeding solution on two sides by two nanoporous membranes. FIG. 8 depicts this apparatus.

EXAMPLE 4

The Three-Sided Apparatus with Channel

Figure 9:
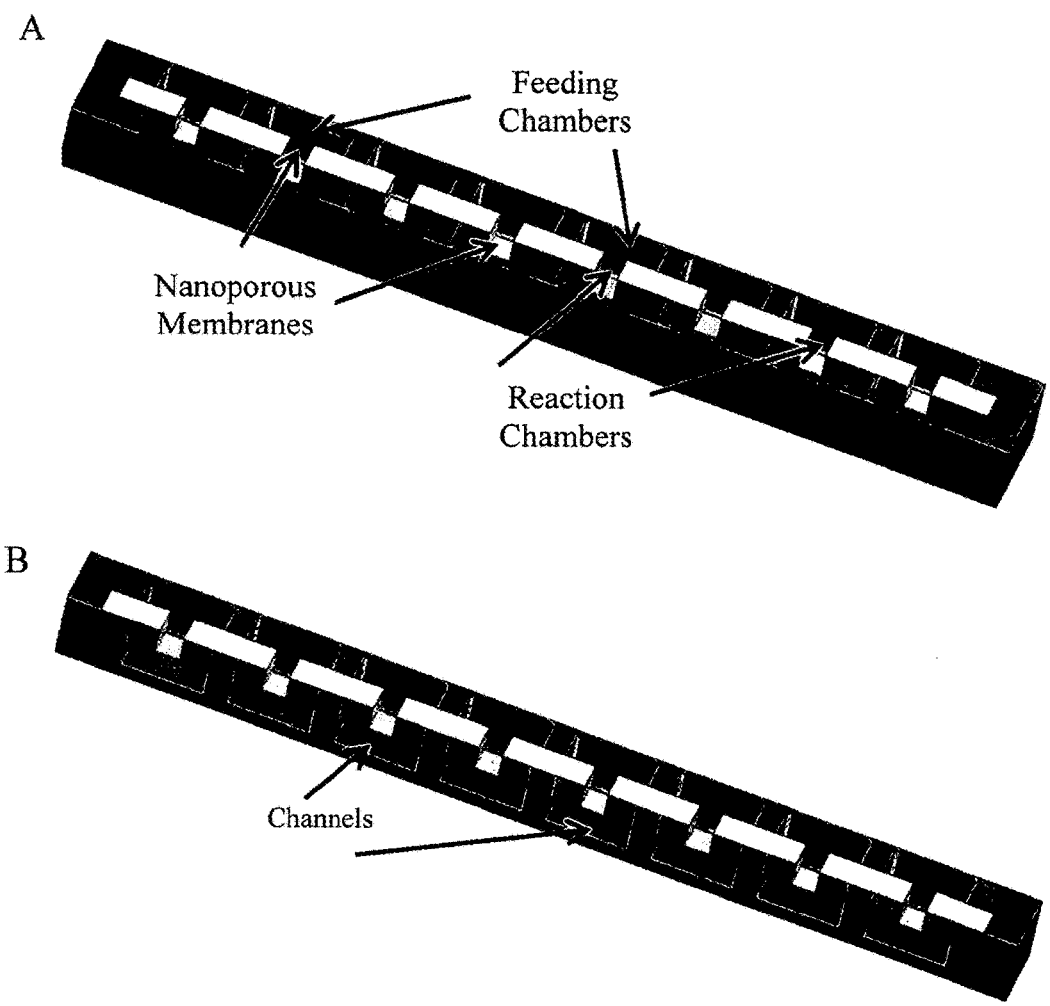
FIGS. 9A-9B. 3-D renderings of the three-sided apparatus with channel. A. An illustration of the entire apparatus with the reaction chambers, feeding chambers, and nanoporous membranes identified. B. Cross-sectional view of the apparatus with the channels identified.

With this apparatus, the reaction solution is separated from the feeding chamber on three sides by nanoporous membranes. This separation includes the two included with the original device plus a membrane separating the reaction solution in the reaction chambers from the feeding solution located in the channel connecting the two feeding chambers beneath the reaction chambers. FIG. 9 illustrates this device. This can be extended to 4 sides. Through injection molding, either a circle shape or square or rectangular shape can be formed.

EXAMPLE 5

The Semi-Continuous Chemical Exchange Apparatus

Figure 10:
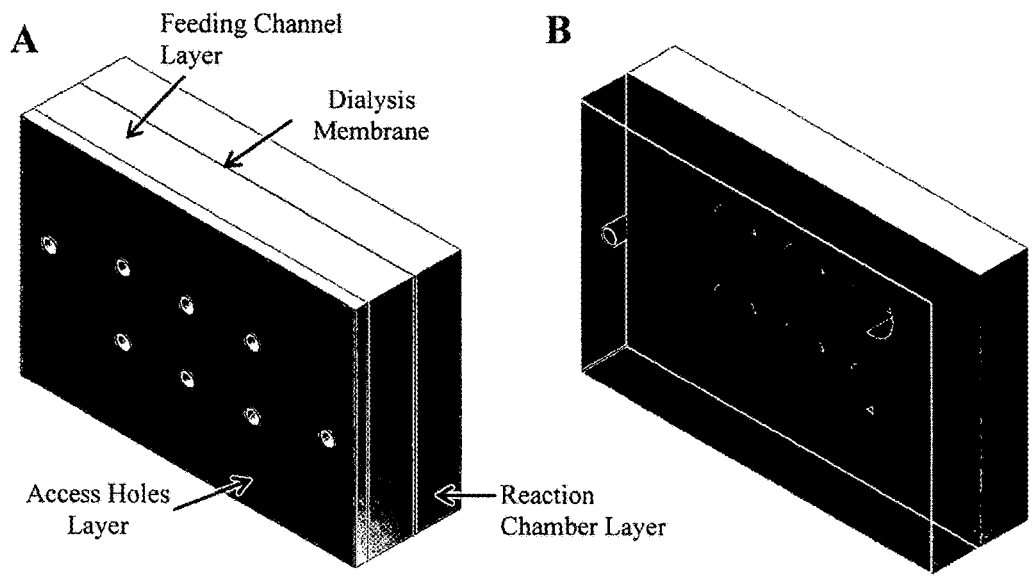
FIGS. 10A-10B. 3-D renderings of an example of semi-continuous chemical exchange apparatus of current invention. A. An illustration of the apparatus with the access holes layer, feeding channel layer, dialysis membrane, and reaction chamber layer identified. B. The apparatus without the top layer. The blue represents the feeding channel layer, and the gray is the reaction chamber layer.
Figure 11:
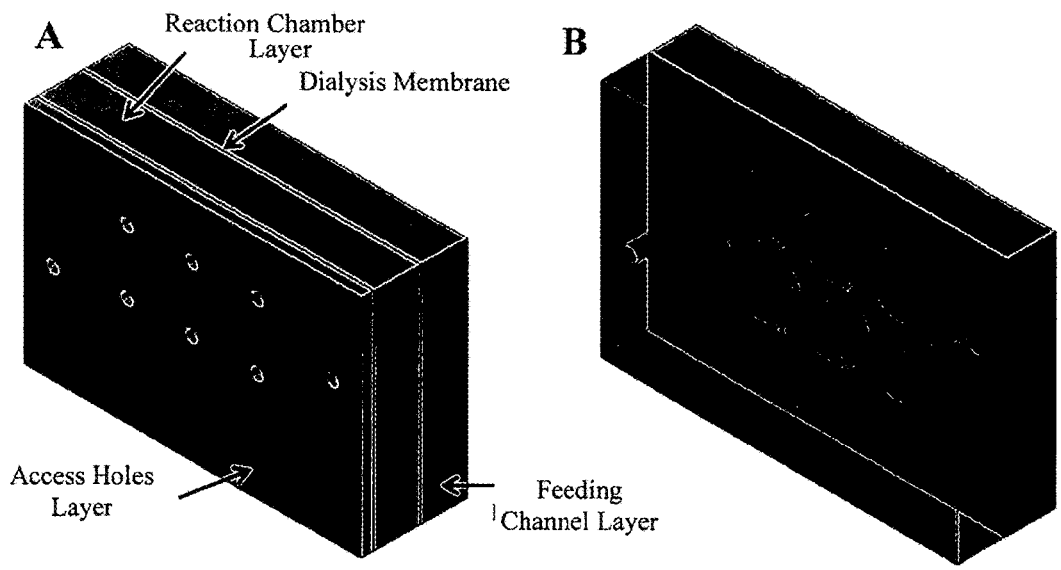
FIGS. 11A-11B. 3-D renderings of an example of semi-continuous chemical exchange apparatus of the current invention. A. An illustration of the entire device with the access holes layer, reaction chamber layer, dialysis membrane, and feeding channel layer identified. B. The apparatus without the top layer. The blue represents the reaction chamber layer, and the gray is the feeding channel layer.

For protein synthesis in a semi-continuous chemical exchange apparatus, feeding solution is actively pumped through a feeding solution channel such that feeding solution is continuously supplied. However, chemical exchange between the feeding channel and reaction chambers occurs passively through diffusion. The feeding channel and reaction chambers are separated by a vertically-oriented nanoporous membrane. This apparatus can be designed in several variations, two of which are depicted in FIGS. 10 and 11. These apparatuses are made up of three layers: an access holes layer that provides access to the feeding channel and reaction chambers, a feeding channel layer, and a reaction chamber layer. The feeding channel layer and reaction chamber layer are separated by a nanoporous membrane. The location of the feeding channel and reaction chamber layers are different between the apparatuses depicted in FIG. 10 and FIG. 11.

EXAMPLE 6

Apparatuses for High Throughput DNA Synthesis

Certain embodiments of the current invention provide apparatuses for high throughput DNA synthesis. The basic fabrication and assembly of the apparatuses for high throughput DNA synthesis is similar to the Vertical Apparatuses I and II described above in Example 1.

To use Vertical Apparatuses I and II for high throughput DNA synthesis, certain modifications are performed on these apparatuses. For example, the feeding solution contains reagents required for synthesis of DNA by polymerase chain reaction. These reagents include, but are not limited to, deoxynucleoside triphosphates (dNTPs), divalent cations (e.g. $MgCl_2$ or $MnCl_2$), monovalent cations (e.g. $K^+$ ions), and buffering reagents. The reaction solution contains reagents that include, but are not limited to, template DNA, primers, and DNA polymerase.

For high throughput DNA synthesis, the Vertical Apparatuses I or II are subjected to thermocycling conditions. Thermocycling conditions comprise subjecting the PCR reaction mixture to denaturation temperature, annealing temperature, and amplification temperature. Various alternatives of thermocycling conditions are well known to a person of ordinary skill in the art and these conditions are within the purview of the current invention.

In an embodiment of the current invention, DNA molecules having different sequences can be synthesized in the plurality of reaction chambers present in the Apparatus of the current invention. For example, different reactions chambers can contain different template DNA or primers to synthesize DNA molecules with different sequences.

EXAMPLE 7

Apparatuses for High Throughput Binding Assays

Certain embodiments of the current invention provide apparatuses for high throughput binding assays, for example, DNA hybridization assays or protein interaction assays. The basic fabrication and assembly of the apparatuses for high throughput binding assays is similar to the Vertical Apparatuses I and II described above in Example 1.

To use Vertical Apparatuses I and II for high throughput binding assays, certain modifications are performed on these apparatuses. For example, the feeding solution can contain reagents that affect binding reactions. For DNA binding assays, these reagents include, but are not limited to, salts that affect stringency of DNA hybridization, buffering reagents, other chemicals that affect stringency of DNA hybridization, markers indicative of the presence of absence of DNA hybridization, etc. The reaction solution can contain reagents that include, but are not limited to, template DNA, probe DNA, markers indicative of the presence of absence of DNA hybridization.

In an embodiment of the current invention, DNA molecules having different sequences can be hybridized with different probes in the plurality of reaction chambers present in the Apparatus of the current invention. For example, different reactions chambers can contain template DNA or probe DNA molecules with different sequences.

EXAMPLE 8

CFPS in µFAD

Cell-free protein synthesis (CFPS) has been used as an alternative to cell-based recombinant technology for protein production. This embodiment of the current invention provides CFPS in a miniaturized well array device that integrated microchannels and nanoporous membranes for continuous supply of a nutrient solution and removal of inhibitory byproducts for higher synthesis yield. The protein synthesis yield in a device with its membrane oriented vertically was more than two times higher than a device with its membrane oriented horizontally, a surprising and unexpected finding. The reaction kinetics of β-glucuronidase expression is also two times faster. Further, the integrated device is compatible with commercial reagent dispensers and microplate readers of a 96-well plate for high-throughput applications.

As discussed above, conventional CFPS systems lack individual element details and thus have limited reagent control for expression optimization. An embodiment of the current invention provides Protein synthesis Using Recombinant Elements (PURE) system which comprises 108 known elements that can be optimized for maximal protein expression yield. These components, including factors, enzymes, and ribosomes, are purified from *E. coli* cells while nuclease and protease activities are reduced to provide greater stability for protein synthesis. With the PURE System, all elements are known, nuclease and protease activity are reduced, and the concentration of each element can be optimized for maximal protein expression. However, protein expression yield with this system is relatively low due to the consumption of nutrients and energy molecules as well as the accumulation of inhibitory byproducts in the batch format. An embodiment of the claimed invention provides µFAD to enhance protein expression with the PURE System. The high-throughput capability enabled by µFAD provides an efficient way to optimize the feeding solution formulation; and the integration of the feeding solution with PURE System significantly enhanced its synthesis yield due to continuous replenishment of nutrients/energy molecules. Consequently, the synthesis yield of green fluorescent protein (GFP) increased 72.5-fold in comparison with the same reaction in the conventional batch format.

The PURE System was developed as a batch-format CFPS system and has relative low protein expression yield due to the consumption of nutrient/energy and the accumulation of inhibitory byproduct. In this work, we aimed to enhance the protein expression yield for the PURE System by developing a system-specific feeding solution, applying this feeding solution to a CECF format device, and optimizing the energy and nutrient concentrations for maximal protein expression yield.

CFPS Format Comparison

Initially, the feeding solution was developed based on the buffer solution components and concentrations included in the PURE System as outlined in Table 2.

Using this initial feeding solution, green fluorescent protein (GFP) was expressed in a conventional microplate and the µFAD, shown in FIG. 14. The expression yield was quantified by the measured fluorescent signal, and the yields were then compared for the PURE System between the batch format (microplate) and CECF format (µFAD). Two batch formats were carried out. The normal batch format was to add 10 µl of the reaction solution to a single well of a conventional microplate. In the enhanced batch condition, 10 µl of reaction solution and 200 µl of feeding solution were added to a single well of a conventional microplate to determine the effects of increased energy and nutrients on protein expression.

Figure 15:
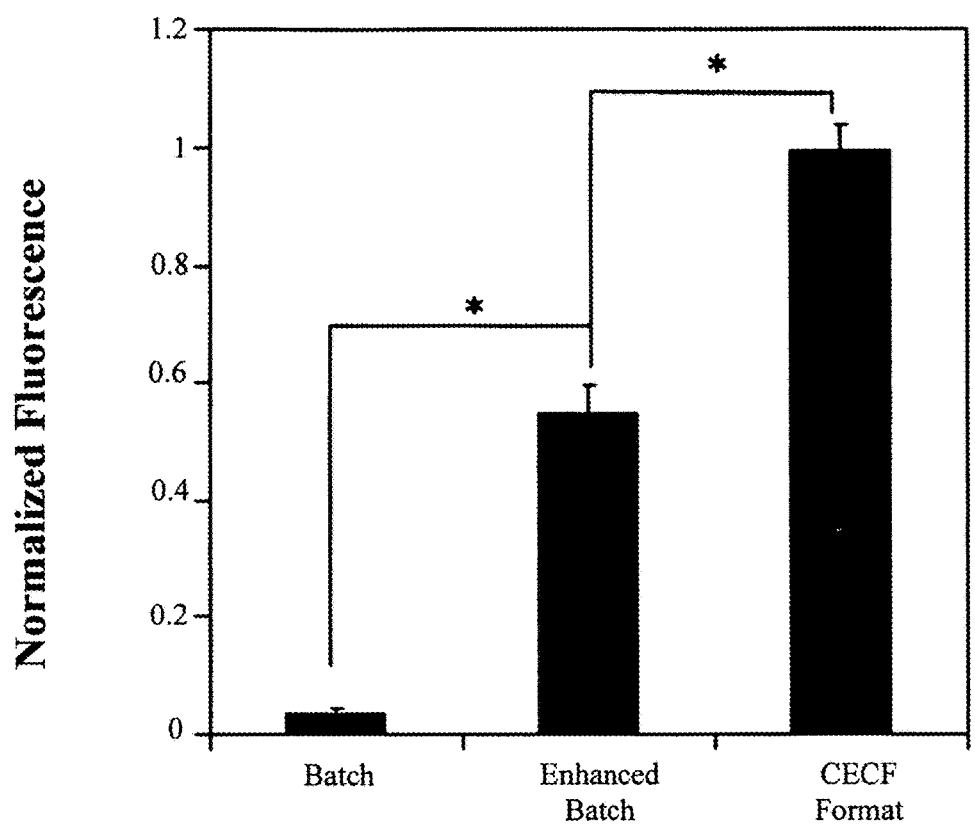
FIG. 15. CFPS format comparison in terms of the GFP expression yield among the batch format (96-well conventional microplate) with the reaction solution only, batch format with the feeding solution added (enhanced batch), and the CECF format (in μFAD). Each experiment was repeated in triplicate, and the error bars represent one standard deviation. The results are normalized against the fluorescent yield in μFAD. The (*) indicates a p-value less than 0.01 for the identified comparisons.

The results of these experiments are shown in FIG. 15, and we observed a 10.6-fold and 20.8-fold increase in protein expression yield in the enhanced batch and CECF formats, respectively, over the batch format. The increase in the protein expression yield from the batch to enhanced batch formats indicates that rapid consumption of energy and nutrients occurs in the batch format. By enhancing the batch format with the feeding solution, additional energy and nutrient molecules are provided to further protein expression. However, while the addition of more energy and nutrient molecules increases protein expression yield, the format is still in batch, and as a result, the rapid accumulation of inorganic phosphate byproducts halts protein expression. In addition, those components existing only in the reaction solution are diluted as a result of adding the feeding solution, further reducing the effects of additional energy molecules. The protein expression yield is further enhanced by allowing a controlled exchange of chemicals between the feeding and reaction solutions across the dialysis membranes in the CECF format. The further increase in the µFAD over the enhanced batch format is due to the fact that the µFAD allows continuous supply of the reactants and removal of the byproducts, rather than diluting critical components (e.g. polymerase) when the feeding solution was pre-mixed into the reaction solution.

Feeding Solution Optimization

As illustrated in FIG. 14b, the chemical exchange between the reaction and feeding solutions in the µFAD is the result of developing concentration gradients across the dialysis membranes during protein expression. For the species highlighted in the figure, accumulating inorganic phosphate byproducts will move from the reaction solution to the feeding solution while ATP, GTP, creatine phosphate, amino acids, and magnesium ions will diffuse into the reaction solution as these elements are consumed during protein expression. Since the accessible amount of the feeding solution components, specifically the energy and nutrient reagents, have effects on protein expression yield, we optimized the concentrations of creatine phosphate, ATP, GTP, magnesium acetate, and amino acids in the feeding solution for maximal protein expression. The concentrations of these components were not altered in the reaction solution since they had been previously optimized, and the concentrations of all other reagents in the feeding solution remained constant to prevent upsetting the optimized pH buffer, salt, and reagent stabilization conditions in the reaction solution. For all optimization studies, the resulting fluorescence is normalized to the protein expression yield for the initial feeding solution conditions of 20 mM creatine phosphate, 2 mM ATP, 2 mM GTP, 13 mM magnesium acetate, and 0.3 mM amino acids.

Feeding solution optimization began with the secondary energy source. In the PURE System, creatine phosphate is the secondary energy source, and it requires the enzymatic action of creatine kinase to transfer its high-energy phosphate group to ADP and GDP, regenerating ATP and GTP during protein translation. The concentration of creatine phosphate in the feeding solution was varied from 10 to 50 mM, and the subsequent protein expression yield was quantified fluorescently. The results for this optimization are shown in FIG. 16a and indicate that the optimal creatine phosphate concentration is 20 mM as we used for the initial feeding solution.

Figure 16A:
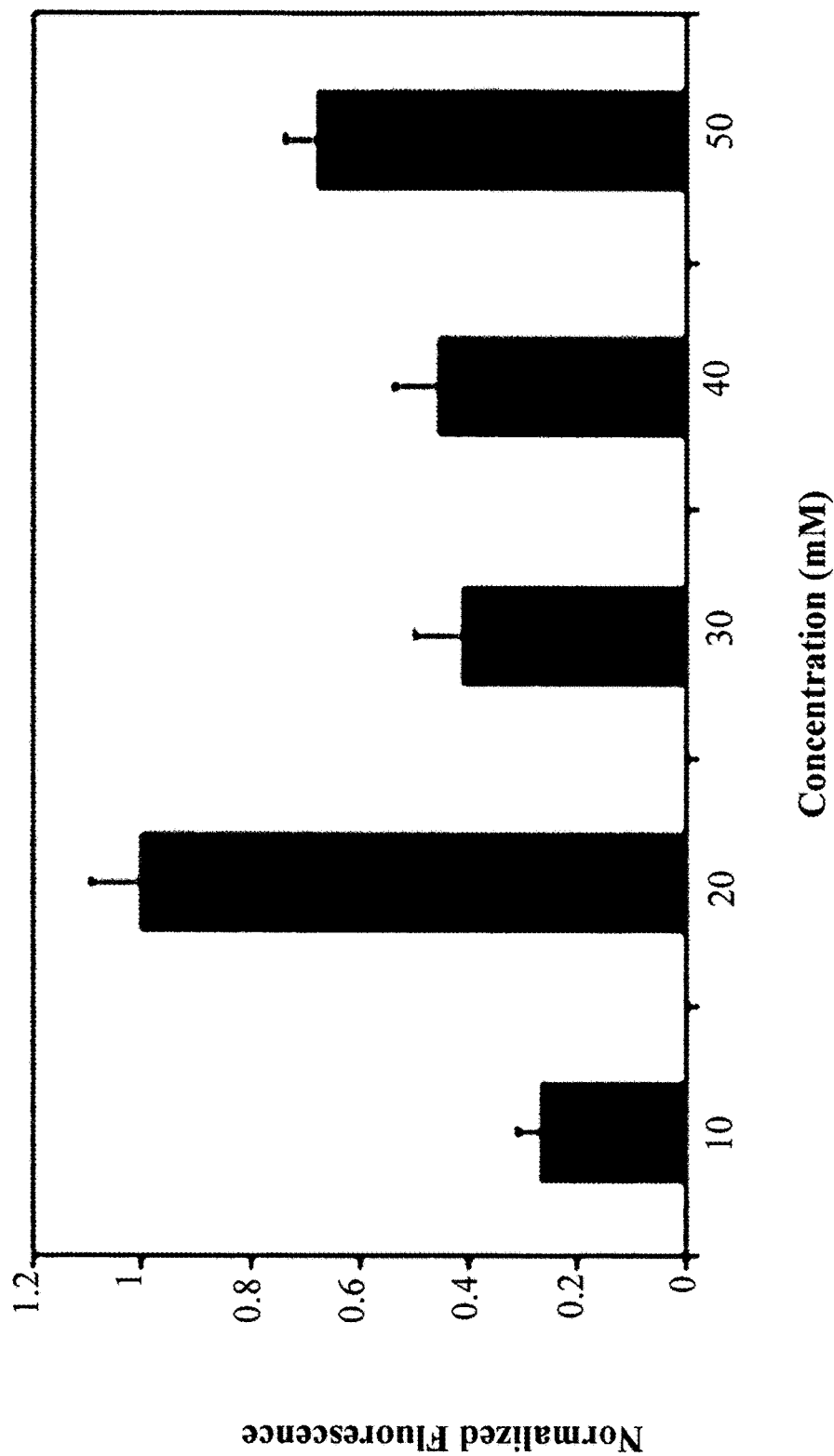
FIGS. 16A-16D. Feeding solution optimization results for (A) creatine phosphate, (B) ATP and GTP, (C) magnesium acetate (MgOAc), and (D) amino acids. Each experiment was repeated in triplicate, and the error bars represent one standard deviation. The results are normalized against the fluorescent yield for the original feeding solution concentrations (20 mM for creatine phosphate, 2 mM for ATP, 2 mM for GTP, 13 mM for magnesium acetate, and 0.3 mM for amino acids).

The result of FIG. 16a may be explained by the fact that that protein expression termination occurs as a tradeoff between two factors: the availability of energy molecules and accumulation of inorganic phosphate byproducts. As mentioned above, creatine phosphate functions as an energy source, but it also helps pyrophosphatase in the reaction solution to catalyze inorganic phosphate molecules. Note that the pyrophosphatase concentration was previously optimized for the PURE System and no additional pyrophosphatase was added to the feeding solution. As a result, the creatine phosphate turnover capability in the CECF format is already determined by the concentrations of creatine kinase and pyrophosphatase in the reaction solution. The results in FIG. 16a indicate that the amount of energy molecules is not sufficient to support the energy requirements of the protein synthesis reaction when creatine phosphate concentration is at 10 mM, causing lower protein expression. When creatine phosphate concentrations are greater than 20 mM, protein expression is also not maximized, which can be explained by two possible reasons. First, protein expression does improve with an increase in creatine phosphate concentration due to the increased energy molecule availability. However, by increasing the concentration of creatine phosphate, the concentration of inorganic pyrophosphate byproducts also increases, which are known to complex with magnesium ions. These inorganic phosphate molecules overwhelm the pyrophosphatase molecules in the reaction solution. As a result, the inorganic phosphate molecules and free creatine phosphate molecules sequester magnesium ions, limiting protein expression. Secondly, like inorganic phosphate, creatine phosphate also has a high affinity for magnesium ions and will reduce magnesium ion availability with greater concentrations. Consequently, the optimized creatine phosphate concentration was selected to be 20 mM, and the optimization of ATP, GTP, magnesium acetate, and amino acids was accomplished based on this concentration. It should be noted that the optimal creatine phosphate concentration for a non-PURE System was reported to be between 30-50 mM.

Figure 16B:
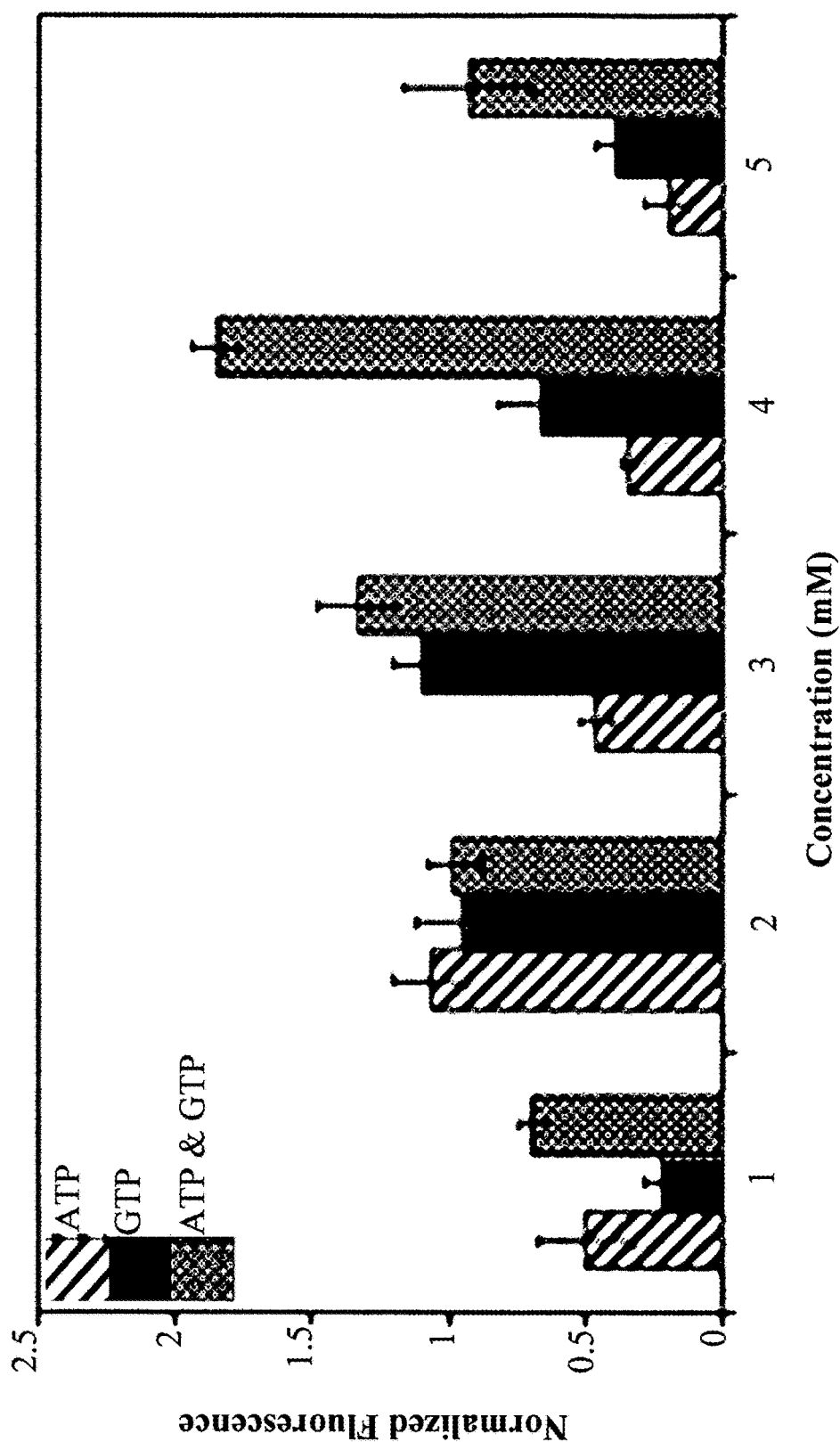

The optimal concentrations of ATP and GTP were investigated by varying the concentrations of these species from 1 to 5 mM. This was first done by varying the concentration of ATP and GTP separately while maintaining a constant concentration for the other species. Then, the concentrations of both ATP and GTP were varied simultaneously. This was explored due to the dual roles of ATP and GTP during protein expression as nucleotides for DNA transcription and energy sources for protein translation. As energy sources, ATP and GTP support different stages of protein translation with ATP being involved in tRNA aminoacylation and GTP propelling polypeptide chain formation in the ribosome; however, these stages are linked with the concentration of aminoacylated tRNA affecting the extent of polypeptide chain formation. The ATP and GTP optimization results, shown in FIG. 16b, support this connection of protein translation stages with the greatest protein expression occurring when the ATP and GTP concentrations are equal. The results indicate that the optimal concentrations for the feeding solution are 4 mM for ATP and 4 mM for GTP. Note that again these optimal ATP and GTP concentrations for the PURE System are different from the reported optimal concentrations of 1.2 mM for ATP and 0.85 mM for GTP for a non-PURE System.

Figure 16C:
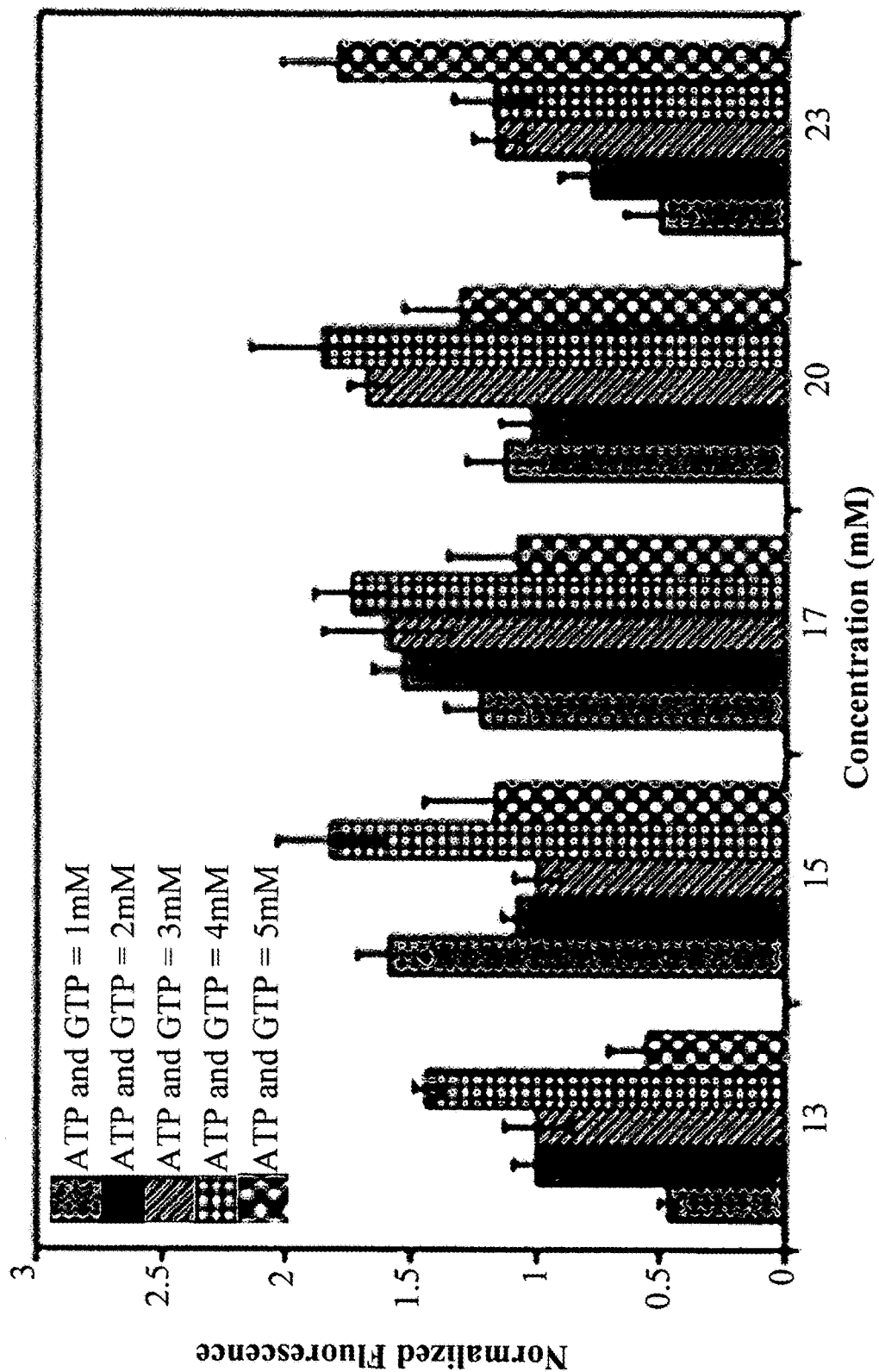

Following ATP and GTP concentration optimization, the concentration of magnesium acetate, which serves as the magnesium ion source, was similarly optimized by varying its concentration from 13 to 23 mM. Magnesium ions serve several functions during protein expression including maintaining ribosome structure and enzymatic activity; in particular, magnesium ions are essential for activating ATP and GTP. However, their availability is often hindered by the presence of compounds with high affinity for magnesium ions such as inorganic phosphate and creatine phosphate. As a result, the concentration of magnesium acetate was optimized in relation to the concentrations of ATP and GTP. The results from this optimization are shown in FIG. 16c. A direct relationship between ATP and GTP concentrations and magnesium acetate concentration was observed, with an increase in the ATP and GTP concentrations requiring a greater concentration of magnesium acetate. In addition, these results indicate that there are multiple optimal magnesium acetate, ATP, and GTP concentration cases. At ATP concentration of 4 mM and GTP concentration of 4 mM, the magnesium acetate concentration can range from 15 mM to 20 mM since there are no statistically significant differences among the expression yields for magnesium acetate at 15, 17, and 20 mM. The expression yield is also at the similar optimum level when magnesium acetate concentration is at 23 mM, ATP concentration at 5 mM, and GTP concentration at 5 mM.

Figure 16D:
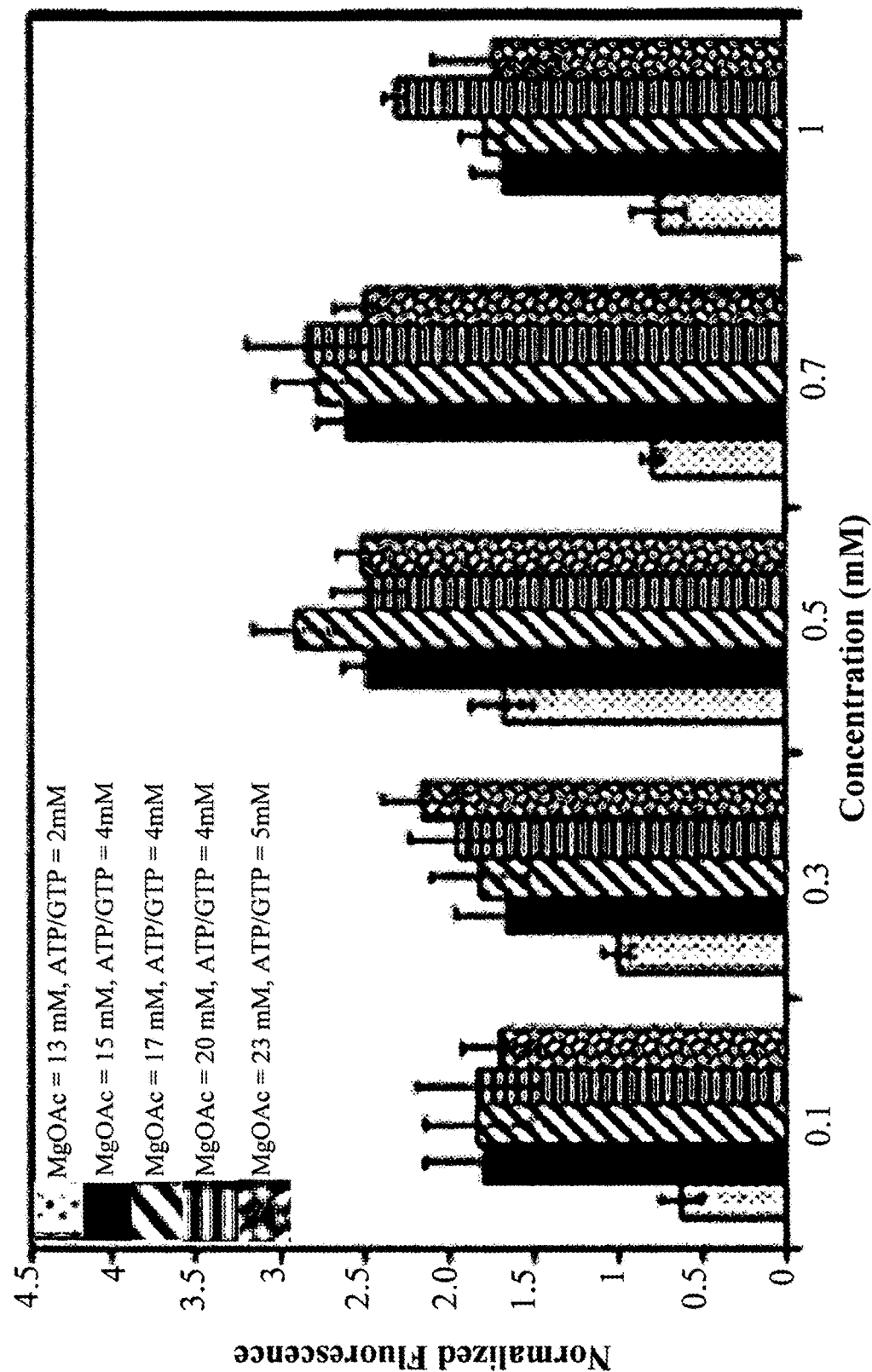

Finally, the concentration of the 20 amino acids was investigated for the four optimal cases from the magnesium acetate concentration optimization study. Each amino acid is supplied in the same concentration for each experiment just as described by Shimizu et al. (2005). Note that the optimal amino acid concentration is dependent on the availability of ATP, GTP, tRNA synthetases, and tRNA. Since the concentrations of reaction solution components were previously optimized in Shimizu et al. (2005) the concentrations of tRNA synthetases and tRNA were not altered. For comparison, the concentration of amino acids was also studied for the original feeding solution composition with ATP concentration of 2 mM, GTP concentration of 2 mM, and magnesium acetate concentration of 13 mM. For each case, the concentration of amino acids were varied from 0.1 to 1 mM and the results are shown in FIG. 16d. Based on these results, the optimized feeding solution should contain 20 mM creatine phosphate, 4 mM ATP, 4 mM GTP, 17 mM magnesium acetate, and 0.5 mM amino acids. The final concentrations of all elements for the optimized feeding solution are listed in Table 2.

Protein Synthesis Yield

Figure 17:
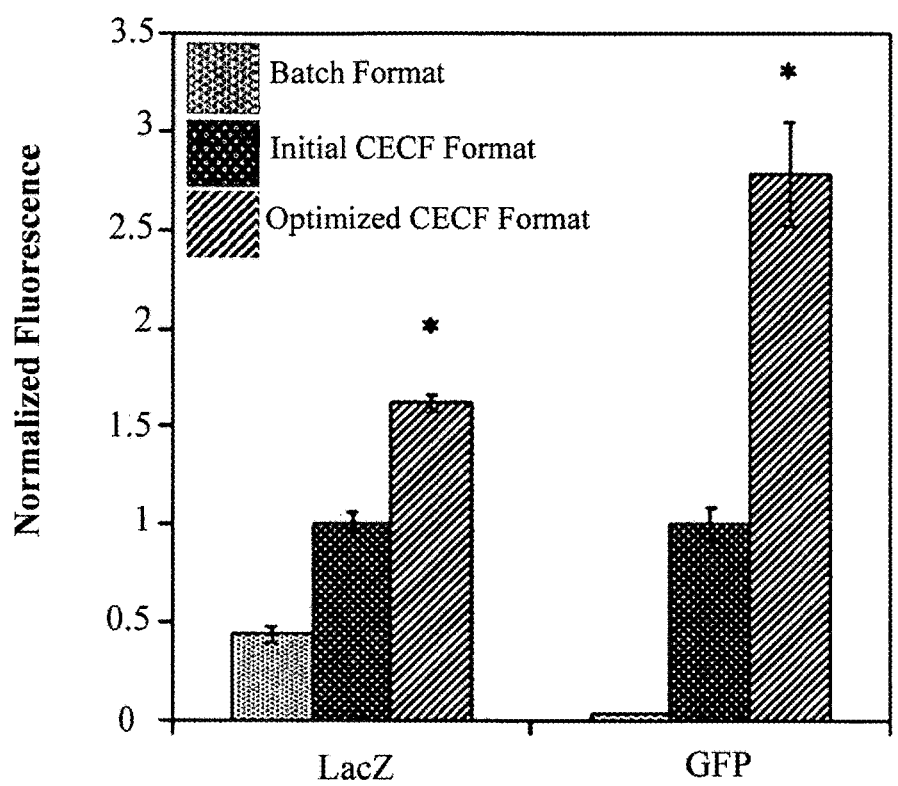
FIG. 17. Comparison in LacZ and GFP expression between the batch and CECF format with either the initial or optimized feeding solution. Each experiment was repeated in triplicate, and the error bars represent one standard deviation. The results are normalized against the expression yield in µFAD with the initial, non-optimized feeding solution. The (*) indicates a p-value less than 0.01 between the initial and optimized CECF formats.

Following feeding solution optimization, GFP and a second protein, β-galactosidase (LacZ), were expressed in the batch format in the conventional microplate and μFAD with the initial and optimized feeding solutions. The resulting protein expression yields were quantified by measuring their fluorescence signals and the comparison are illustrated in FIG. 17. Compared to the batch format and the initial feeding solution, the optimized feeding solution enhances protein expression yield for both proteins. For GFP expression, the optimized feeding solution with μFAD increased the synthesis yield by 72.5-fold and 2.8-fold, respectively, over the batch and CECF format with the initial feeding solution. Based on a calibration curve for rGFP (FIG. 13), 2.8 μg/ml of GFP is expressed in the batch format. By transitioning to a CECF format, GFP productivity increases to 48.8 μg/ml with the initial feeding solution and to 144.5 μg/ml with the optimized feeding solution. Additionally, protein expression yield of LacZ showed a similar trend for the optimized feeding solution with a 5.9-fold and 1.4-fold increase, respectively, over the batch format and CECF format with the initial feeding solution.

Reaction Time Dependence

Figure 18:
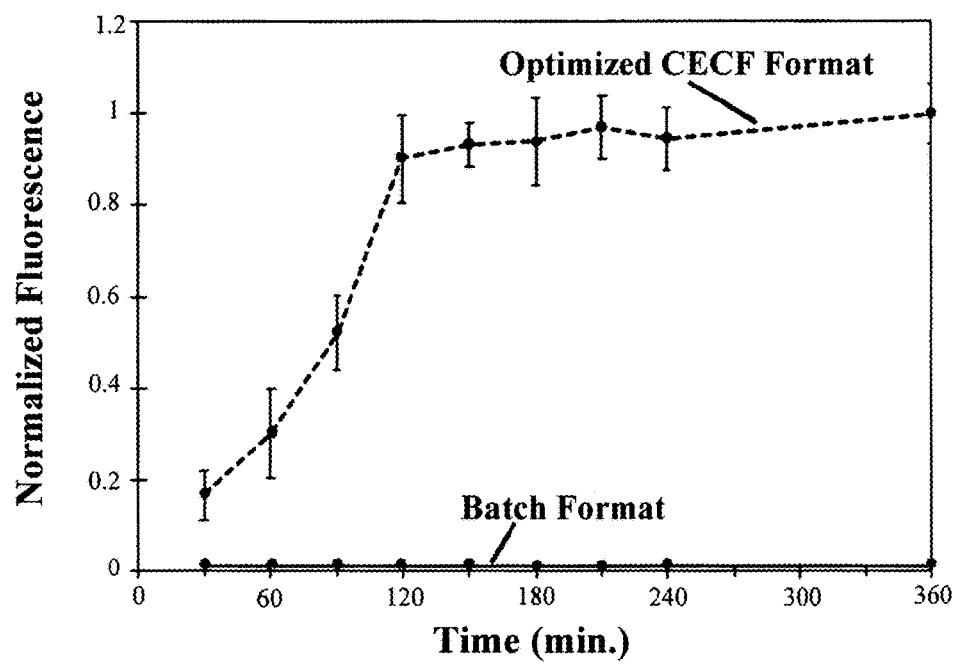
FIG. 18. GFP expression monitored every 30 minutes for four hours in the batch and optimized CECF formats. The experiment was repeated in triplicate, and the error bars represent one standard deviation. The results are normalized against the greatest expression yield time point in the µFAD.

With the CECF format, the observed increase in the protein expression yield can be partially attributed to an increase in the reaction time as a result of the controlled chemical exchange across the dialysis membrane. This was confirmed by monitoring GFP expression every half an hour for four hours for the batch format and CECF format with the optimized feeding solution. The results are depicted in FIG. 18. The protein synthesis yield in the batch format reached a plateau at 0.5 hours, but it continued for an additional 1.5 hours in the μFAD.

Thus, this embodiment of the current invention provides optimized feeding solution specific to the PURE System using a μFAD that is in a 96-well CECF format. Compared to the traditional batch format, a CECF format device increases protein expression by enabling continuous supply of nutrients and energy molecules from a feeding solution and removal of accumulating inorganic phosphate byproducts from the reaction solution. This enhanced protein expression was observed even with the non-optimized feeding solution, which was based on the previously used buffer and energy reagent concentrations. The GFP expression yield in the μFAD increased 20.9 times over the traditional batch format. The optimized feeding solution comprises 20 mM creatine phosphate, 4 mM ATP, 4 mM GTP, 17 mM magnesium acetate, and 0.5 mM amino acids increased GFP and LacZ expression 72.5-fold and 5.9-fold, respectively, in comparison with the batch format. In addition, the CECF format increased the protein reaction time from 0.5 hours for the batch format to 2 hours, contributing to the observed protein expression yield enhancement.

As such, this embodiment of the invention provides the CECF format as well as the use of a feeding solution in providing a means for the continuous supply of vital nutrient and energy molecules and removal of inhibitory inorganic phosphate byproducts to maximize protein expression. The μFAD described in this embodiment of the current invention provides a high-throughput platform for efficient optimization of the feeding solution components, and can be used for simultaneous production of up to 96 proteins.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. S. Gräslund, R. Hui, J. Ming, S. dhe-Paganon, H. W. Park, A. Savchenko, A. Yee, A. Edwards, R. Vincentelli, C. Cambillau, R. Kim, P. Nordlund, S. H. Kim, Z. Rao, Y. Shi, T. C. Terwilliger, C. Y. Kim, L. W. Hung, G. S. Waldo, Y. Peleg, S. Albeck, T. Unger, J. Weigelt, O. Dym, J. Prilusky, J. L. Sussman, R. C. Stevens, S. A. Lesley, I. A. Wilson, A. Joachimiak, F. Collart, I. Dementieva, M. I. Donnelly, B. M. Hallberg, W. H. Eschenfeldt, Y. Kim, L. Stols, R. Wu, M. Zhou, S. K. Burley, J. S. Emtage, J. M. Sauder, D. Thompson, K. Bain, J. Bray, J. Luz, T. Gheyi, F. Zhang, S. Atwell, S. C. Almo, J. B. Bonanno, A. Fiser, S. Swaminathan, F. W. Studier, M. R. Chance, O. Gileadi, A. Sali, T. B. Acton, R. Xiao, L. Zhao, L. C. Ma, J. F. Hunt, L. Tong, K. Cunningham, M. Inouye, S. Anderson, S. Knapp, H. Janjua, R. Shastry, C. K. Ho, D. Wang, H. Wang, M. Jiang, G. T. Montelione, D. I. Stuart, R. J. Owens, S. Daenke, U. Oppermann, A. Schutz, U. Heinemann, S. Yokoyama, K. Büssow, K. C. Gunsalus, and C. Arrowsmith, Nat. Methods., 2008, 5, 135-146.
2. Y. Shimizu, Y. Kuruma, B. W. Ying, S. Umekage, and T. Ueda, FEBS J., 2006, 273, 4133-4140.
3. M. He, New Biotech., 2008, 25, 126-132.
4. M. He, Y. He, Q. Luo, and M. Wang, Process Biochem., 2011, 46, 615-620.
5. H. Nakano, and T. Yamane, Biotech. Adv., 1998, 16, 367-384.
6. F. Katzen, G. Chang, and W. Kudlicki, Trends Biotechnol., 2005, 23, 150-156.

7. V. A. Shirokov, P. N. Simonenko, S. V. Biryukov, and A. S. Spirin in Cell-free translation systems, ed. A. Spirin, Springer, Berlin, 2002, p. 91-107.
8. M. Watanabe, K. Miyazono, M. Tanokura, T. Sawasaki, Y. Endo, and I. Kobayashi, Methods Mol. Biol., 2010, 607, 149-160.
9. E. H. Morita, T. Sawasaki, R. Tanaka, Y. Endo, and T. Kohno. Protein Sci., 2003, 12, 1216-1221.
10. P. Avenaud, M. Castroviejo, S. Claret, J. Rosenbaum, F. Megraud, and A. Ménard. Biochem. Biophys. Res. Commun., 2004, 318, 739-745.
11. H. Chen, X. Yan, F. Tian, Y. Song, Y. Q. Chen, H. Zhang, and W. Chen, Biotechnol. Lett., 2012, 34, 359-364.
12. Q. Mei, W. Fredrickson, S. Jin, S., and Z. H. Fan, Anal. Chem., 2005, 77, 5494-5500.
13. Q. Mei, C. K. Fredrickson, W. Lian, S. Jin, and Z. H. Fan, Anal. Chem., 2006, 78, 7659-7664.
14. Y. V. Svitkin and N. Sonenberg, Methods Enzymol., 2007, 429, 53-82.
15. R. Khnouf, D. Olivero, S. Jin, M. A. Coleman, and Z. H. Fan, Biotechnol. Prog., 2010, 26, 1590-1596.
16. R. Khnouf, D. Olivero, S. Jin, and Z. H. Fan, Anal. Chem., 2010, 82, 7021-7026.
17. T. Sawasaki, T. Ogasawara, R. Morishita, and Y. Endo, Proc. Natl. Acad. Sci. USA, 2002, 99, 14652-14657.
18. T. Kigawa, Methods Mol. Biol., 2010, 607, 53-62.
19. A. S. Spirin, V. I. Baranov, L. A. Ryabova, S. Y., and Y. B. Alakhov, Science, 1988, 242, 1162-1164.
20. L. A. Ryabova, I. Y. Morozov, and A. S. Spirin, Molecular Biology, 1998, 77, 179-193.
21. D. M. Kim, and C. Y. Choi, Biotechnol. Prog., 1996, 12, 645-649.
22. Q. Mei, C. K. Fredrickson, A. Simon, R. Khnouf, R., and Z. H. Fan, Biotechnol. Prog., 2007, 23, 1305-1311.
23. D. S. Tawfik, and A. D. Griffiths, Nat. Biotech, 1998, 16, 652-656.
24. T. Osaki, S. Yoshizawa, R. Kawano, H. Sakai, and S. Takeuchi, Anal. Chem., 2011, 83, 3186-3191.
25. S. Y. Teh, R. Khnouf, H. Fan, and A. P. Lee, Biomicrofluidics, 2011, 5, 044113.
26. N. Park, S. H. Um, H. Funabashi, J. Xu, and D. Luo, Nature Materials, 2009, 8, 432-437.
27. P. Angenendt, L. Nyarsik, W. Szaflarski, J. Glokler, K. H. Nierhaus, H. Lehrach, D. J. Cahill, and A. Lueking, Anal. Chem., 2004, 76, 1844-1849.
28. G. H. Hahn, A. Asthana, D. M. Kim, and D. P. Kim, Anal. Biochem., 2007, 365, 280-282.
29. B. H. Chueh, D. Huh, C. R. Kyrtsos, T. Houssin, N. Futai, and S. Takayama, Anal. Chem., 2007, 79, 3504-3508.
30. A. S. Spirin and J. R. Swartz, in *Cell-Free Protein Synthesis*, ed. A. S. Spirin and J. R. Swartz, WILEY-VCH Verlag GmbH & Co. KGaA, Weinheim, 2008, ch. 1, pp. 1-34.
31. A. S. Spirin, *Trends Biotechnol.*, 2004, 22, 538-545.
32. T. Stogbauer, L. Windhager, R. Zimmer and J. O. Radler, *Integrative Biology*, 2012, 4, 494-501.
33. M. He, O. Stoevesandt, E. A. Palmer, F. Khan, O. Ericsson and M. J. Taussig, *Nature Methods*, 2008, 5, 175-177.
34. S. Kubick, M. Gerrits, H. Merk, W. Stiege and V. A. Erdmann, *Membrane Protein Crystallization*, 2009, 63, 25-49.
35. N. Wu, Y. Zhu, S. Brown, J. Oakeshott, T. S. Peat, R. Surjadi, C. Easton, P. W. Leech and B. A. Sexton, *Lab on a Chip*, 2009, 9, 3391-3398.
36. Y. Shimizu, A. Inoue, Y. Tomari, T. Suzuki, T. Yokogawa, K. Nishikawa and T. Ueda, *Nat. Biotechnol.*, 2001, 19, 751-755.
37. D. M. Kim and J. R. Swartz, *Biotechnol. Bioeng.*, 1999, 66, 180-188.
38. D. M. Kim and J. R. Swartz, *Biotechnol. Prog.*, 2000, 16, 385-390.
39. M. C. Jewett and J. R. Swartz, *Biotechnol. Bioeng.*, 2004, 87, 465-471.
40. N. Michel-Reydellet, K. Calhoun and J. Swartz, *Metab. Eng.*, 2004, 6, 197-203.
41. H. Nakano, T. Shinbata, R. Okumura, S. Sekiguchi, M. Fujishiro and T. Yamane, *Biotechnol. Bioeng.*, 1999, 64, 194-199.
42. M. C. Jewett and J. R. Swartz, *Biotechnol. Bioeng.*, 2004, 86, 19-26.
43. K. A. Calhoun, and J. R. Swartz, *Biotechnol. Bioeng.*, 2005, 90, 606-613.
44. J. A. Cappuccio, C. D. Blanchette, T. A. Sulchek, E. S. Arroyo, J. M. Kralj, A. K. Hinz, E. A. Kuhn, B. A. Chromy, B. W. Segelke, K. J. Rothschild, J. E. Fletcher, F. Katzen, T. C. Peterson, W. A. Kudlicki, G. Bench, P. D. Hoeprich and M. A. Coleman, *Mol. Cell. Proteomics*, 2008, 7, 2246-2253.
45. R. Khnouf, D. Olivero, S. Jin and Z. H. Fan, *Biotechnol. Prog.*, 2010, 26, 1590-1596.
46. Y. Shimizu, T. Kanamori and T. Ueda, *Methods*, 2005, 36, 299-304.
47. Y. Shimizu and T. Ueda, in *Cell-Free Protein Production: Methods and Protocols*, ed. Y. Endo, K. Takai and T. Ueda, Humana Press, New York City, 2010, ch. 2, pp. 11-21.
48. H. Ohashi, Y. Shimizu, B. W. Ying and T. Ueda, *Biochem. Biophys. Res. Commun.*, 2007, 352, 270-276.

We claim:

1. An apparatus comprising a plurality of devices for cell-free protein synthesis, each of the devices comprising:
   a) a reaction chamber,
   b) at least two feeding chambers, and
   c) at least two porous membranes separating the reaction chamber and the at least two feeding chambers, wherein (1) the at least two porous membranes allow passage of certain chemicals between the reaction chamber and the at least two feeding chambers while preventing passage of other chemicals from the reaction chamber and the at least two feeding chambers, and (2) the at least two porous membranes are in substantially vertical position.

2. The apparatus of claim 1, wherein two porous membranes separate the reaction chamber and the at least two feeding chambers in at least one of the devices.

3. The apparatus of claim 2, wherein the at least two feeding chambers are separated from the reaction chamber by a height differential.

4. The apparatus of claim 3, wherein the height differential (Oh) is less than 15.0 mm.

5. The apparatus of any preceding claim, wherein the at least two porous membranes are selected from one or more of the following membranes: size based semipermeable membranes, charge based semipermeable membranes, anion exchange membranes, alkali anion exchange membranes, charge mosaic membranes, or proton exchange membranes.

6. The apparatus of claim 1, wherein each of the devices further comprises one or more channels connected to the at least two feeding chambers, wherein the contents of the at least two feeding chambers can be removed or the contents can be added to the at least two feeding chambers through the one or more channels.

7. The apparatus of claim 5, wherein the semipermeable membrane is a nanoporous membrane or a lipid membrane.

8. The apparatus of claim 1-2, 3-4, or 6, wherein the ratio of the volume of the at least two feeding chambers to the volume of the reaction chamber is about 5:1, about 10:1, about 15:1, about 20:1, about 25:1, or about 30:1.

9. The apparatus of claim 8, wherein the volumes of the at least two feeding chambers and the reaction chamber are about 50 μL and about 10 μL, respectively; about 100 μL, and about 10 μL, respectively; about 150 μL, and about 10 μL, respectively; about 200 μL and about 10 μL, respectively; about 250 μL and about 10 μL, respectively; or about 300 μL and about 10 μL, respectively.

10. The apparatus of claim 8, wherein the volumes of the at least two feeding chambers and the reaction chamber are about 25 μL and about 5 μL, respectively; about 50 μL and about 5 μL, respectively; about 75 μL and about 5 μL, respectively; about 100 μL and about 5 μL, respectively; about 125 μL and about 5 μL, respectively; or about 150 μL and about 5 μL, respectively.

11. A method of synthesizing a product comprising:
providing the apparatus according to any one of claim 1-2, 3-4, or 6;
adding one or more compositions comprising raw materials and, optionally, one or more compositions comprising one or more reagent providing components that are converted into a product produced by said raw materials to the reaction chamber to prepare a reaction mixture, wherein the raw materials are incapable of diffusing through said at least two porous membranes into said at least two feeding chambers;
adding one or more compositions comprising one or more reagent that is converted into a product by said raw materials into said at least two feeding chambers to prepare a feeding solution, wherein said feeding solution is separated from said reaction mixture by said at least two porous membranes; and
providing reaction conditions that permit the synthesis of said product in said reaction chamber.

12. The apparatus of claim 1, wherein the reaction chamber comprises a reaction mixture and the at least two feeding chambers comprise a feeding solution, wherein the ratio of the volume of the feeding solution to the volume of the reaction mixture is about 5:1, about 10:1, about 15:1, about 20:1, about 25:1, or about 30:1.

13. The apparatus of claim 12, wherein the volumes of the feeding solution and the reaction mixture are about 50 μL and about 10 μL, respectively; about 100 μL, and about 10 μL, respectively; about 150 jut and about 10 μL, respectively; about 200 μL and about 10 μL, respectively; about 250 μL, and about 10 μL, respectively; about 300 μL and about 10 μL, respectively, about 600 μL and about 20 μL, respectively; about 1200 μL and about 40 μL, respectively; about 1800 μL and about 60 μL, respectively; about 2400 μL and about 80 μL, respectively; or about 3000 μL and about 100 μL, respectively.

14. The apparatus of claim 12, wherein the volumes of the feeding solution and the reaction mixture are about 25 μL and about 5 μL, respectively; about 50 μL and about 5 μL, respectively; about 75 μL and about 5 μL, respectively; about 100 μL and about 5 μL, respectively; about 125 μL, and about 5 μL, respectively; or about 150 μL and about 5 μL, respectively.

15. The method of claim 11, wherein the product is a protein.

16. The method of claim 15, wherein the protein is synthesized through cell-free protein synthesis.

17. The method of claim 16, wherein the cell free protein synthesis comprises:
a) providing said reaction chamber with raw materials that are not diffusible through said at least two porous membranes, the raw materials comprising DNA or RNA encoding a protein, ribosomes, and translation factors,
b) providing said reaction chamber and/or said at least two feeding chambers with reagents comprising amino acids, and adenosine triphosphate, and
c) providing reaction conditions that permit the synthesis of said protein in said reaction chamber,
wherein, said at least two porous membranes are designed to allow the passage of reagents from said at least two feeding chambers to said reaction chamber and the passage of inhibitory by-products produced during the protein synthesis from said reaction chamber to said at least two feeding chambers while preventing the passage of raw materials comprising DNA or RNA encoding for the protein, ribosomes, and translation factor proteins and the newly synthesized proteins from said reaction chamber to said at least two feeding chambers.

18. The apparatus of claim 12, wherein the reaction chamber provides conditions that permit the synthesis of a protein for about 0.1 hour, about 1 hour, about 10 hour, or about 100 hours.

19. The apparatus of claim 12, wherein the reaction chamber provides conditions that permit the synthesis of a protein at a temperature of about 20° C. to about 45° C., about 25° C. to about 40° C., about 30° C. to about 37° C.

20. The apparatus of claim 12, wherein the reaction chamber provides conditions that permit the synthesis of a protein at a room temperature or a temperature of about 37° C.

21. The method of claim 11, wherein the product is a nucleic acid.

22. The method of claim 21, wherein the nucleic acid is synthesized through polymerase chain reaction.

23. The method of claim 22, wherein the polymerase chain reaction comprises:
a) providing said reaction chamber with raw materials that are not diffusible through said at least two porous membranes, the raw materials comprising template nucleic acids, DNA or RNA polymerase, and primers for the polymerase chain reaction,
b) providing said reaction chamber and/or said at least two feeding chambers with reagents comprising deoxynucleotide triphosphates, adenosine triphosphate, $MgCl_2$, $MnCl_2$, and $K^+$ ions, and
c) providing reaction conditions that permit the synthesis of said DNA through polymerase chain reaction in said reaction chamber,
wherein, said at least two porous membranes are designed to allow the passage of said reagents from said at least two feeding chambers to said reaction chamber and the passage of inhibitory by-products produced during the polymerase chain reaction from said reaction chamber to said at least two feeding chambers while preventing or limiting passage of the raw materials comprising template nucleic acids, DNA or RNA polymerase, and primers for the polymerase chain reaction, and the newly synthesized nucleic acids from said reaction chamber to said at least two feeding chambers.

24. The method of claim 23, wherein the reagents further comprise fluorescent dyes and/or ethidium bromide used for the identification of the newly synthesized nucleic acid.

25. The method of claim 23, wherein the raw materials further comprise probes used in the identification of the newly synthesized nucleic acids.

26. The method of claim 23, wherein providing reaction conditions that permit the synthesis of said DNA through polymerase chain reaction comprises providing thermocycling conditions to said reaction chamber.

27. The method of claim 26, wherein providing thermocycling conditions comprises providing denaturation temperature, annealing temperature, and amplification temperature to the reaction chamber.

28. The method of claim 11, wherein said composition comprising one or more reagent providing components that are converted into a product comprises a reagent selected from: deoxynucleotide triphosphates, adenosine triphosphate, $MgCl_2$, $MnCl_2$, $K^{30}$ ions, amino acids, adenosine triphosphate or any combination thereof.

* * * * *